United States Patent [19]

Hart et al.

[11] Patent Number: 5,328,628
[45] Date of Patent: Jul. 12, 1994

[54] DETERGENT COMPOSITIONS CONTAINING LIPOSOMES AND PROCESS THEREFOR

[75] Inventors: Gerald L. Hart, Surbiton; Anjum F. Ahmed, Virginia Water, both of United Kingdom; Ursula K. Charaf, Racine, Wis.

[73] Assignee: S. C. Johnson & Son, Inc., Racine, Wis.

[21] Appl. No.: 935,688

[22] Filed: Aug. 26, 1992

Related U.S. Application Data

[62] Division of Ser. No. 578,913, Sep. 6, 1990, abandoned.

[51] Int. Cl.$^5$ .................... A61K 9/127; C11D 1/37; C11D 17/08
[52] U.S. Cl. ............................ 252/91; 252/173; 252/174.13; 252/174.16; 252/545; 252/547; 252/550; 252/551; 252/555; 252/DIG. 13; 264/4.3; 424/450; 428/402.2; 514/881
[58] Field of Search .............. 264/4.3; 428/402.2; 424/450; 436/829; 514/78, 881; 252/174.13, 550, 551, 555, 545, DIG. 13, 91

[56] References Cited

U.S. PATENT DOCUMENTS

| | | | |
|---|---|---|---|
| 3,957,971 | 5/1976 | Oleniacz | 424/70 |
| 4,174,296 | 11/1979 | Kass | 252/312 |
| 4,217,344 | 8/1980 | Vanlerberghe et al. | 424/60 |
| 4,224,179 | 9/1980 | Schneider | 424/450 X |
| 4,297,251 | 10/1981 | Bernardino | 252/545 |
| 4,438,052 | 3/1984 | Weder et al. | 264/4.6 |
| 4,483,929 | 11/1984 | Szoka | 436/533 |
| 4,536,324 | 8/1985 | Fujiwara et al. | 252/311 |

(List continued on next page.)

FOREIGN PATENT DOCUMENTS

| | | | |
|---|---|---|---|
| 187702 | 7/1986 | European Pat. Off. | C07C 93/02 |
| 280492 | 8/1988 | European Pat. Off. | A61K 9/56 |

(List continued on next page.)

OTHER PUBLICATIONS

Chemical Abstract No. 103:147164k, Abstract of Japanese Kokai Tokkyo Koho JP 60 72,829 (Apr. 24, 1985).

(List continued on next page.)

Primary Examiner—Richard D. Lovering

[57] ABSTRACT

This invention relates to a method of stabilizing liposomes contained in aqueous compositions against lysis by anionic surfactants otherwise known to disrupt and lyse such liposomes by using certain surfactants as stabilizing agents and to the stabilized compositions obtained thereby as well as to a method of making detergent compositions containing such stabilized liposomes and anionic surfactants as well as to the compositions themselves. The compositions can be used as shower gels and shampoos. The liposomes are preferably vesicles derived from natural phospholipids or from synthetic nonionic amphiphilic compounds which are sometimes referred to as "niosomes" and may contain water soluble humectants or vitamins. From about 0.1% to 40%, and more preferably, from 2% to 10%, by weight of at least one surfactant such as fatty alkyl sulfosuccinates (fatty alkyl group contains from 8 to 22 carbons atoms), fatty acylamino polyglycol ether sulfates (fatty acyl group contains from 8 to 22 carbon atoms), fatty alkyl amine oxides (fatty alkyl group contains from 7 to 26 carbon atoms), fatty alkyl phosphate esters (fatty alkyl group contains from 8 to 22 carbon atoms), and N-acyl amino acid salts or salts of N-acyl derivatives of hydrolyzed proteins of up to about 2,500 daltons in weight average molecular weight (acyl portion is derived from a carboxylic acid having from 8 to 22 carbon atoms) is added to an aqueous composition containing from about 0.1% to 50%, and more preferably from 5% to 30%, by volume of liposomes to produce a stabilized liposome suspension. Such stabilized liposome suspensions can then be included in a detergent formulation containing from about 0.1 to 35%, and more preferably from 5% to 15%, by weight of at least one anionic surfactant which is known to lyse liposomes such as sodium lauryl sulfate or sodium laureth-2 sulfate.

18 Claims, 12 Drawing Sheets

U.S. PATENT DOCUMENTS

| | | | |
|---|---|---|---|
| 4,610,868 | 9/1986 | Fountain et al. | 424/1.1 |
| 4,670,185 | 6/1987 | Fujiwara et al. | 252/311 |
| 4,708,861 | 11/1987 | Popescu et al. | 424/1.1 |
| 4,745,199 | 5/1988 | Carlson | 549/315 |
| 4,752,572 | 6/1988 | Sundberg et al. | 435/7 |
| 4,783,220 | 11/1988 | Gamble et al. | 106/27 |
| 4,793,943 | 12/1988 | Haslop et al. | 252/135 |
| 4,811,791 | 3/1989 | Harnoy et al. | 166/305.1 |
| 4,828,837 | 5/1989 | Uster et al. | 514/78 X |
| 4,830,857 | 5/1989 | Handjani et al. | 424/450 |
| 4,853,228 | 8/1989 | Wallach et al. | 424/450 |
| 4,885,159 | 12/1989 | Miyake et al. | 424/450 X |
| 4,900,556 | 2/1990 | Wheatley et al. | 424/450 |
| 4,911,928 | 3/1990 | Wallach | 424/450 |
| 4,917,951 | 4/1990 | Wallach | 428/402.2 |
| 4,942,038 | 7/1990 | Wallach | 424/450 |
| 4,985,425 | 1/1991 | Chiba et al. | 514/881 X |
| 5,019,394 | 5/1991 | Hamaguchi et al. | 424/450 X |
| 5,032,457 | 7/1991 | Wallach | 428/402.2 |

FOREIGN PATENT DOCUMENTS

| | | | |
|---|---|---|---|
| 88/06882 | 9/1988 | PCT Int'l Appl. | A61K 9/50 |
| 90/01921 | 3/1990 | PCT Int'l Appl. | A61K 7/075 |
| 90/06106 | 6/1990 | PCT Int'l Appl. | A61K 9/18 |
| 91/04013 | 4/1991 | PCT Int'l Appl. | A61K 9/127 |
| 91/04731 | 4/1991 | PCT Int'l Appl. | |
| 2151203 | 1/1987 | United Kingdom | B01J 13/02 |
| 2199494 | 7/1988 | United Kingdom | A61K 7/00 |

OTHER PUBLICATIONS

Chemical Abstract No. 104:10579a, Abstract of Japanese Kokai Tokkyo Koho JP 60 136,508 (Jul. 20, 1985).

English Translation of Article Noted in Chemical Abstract No. 98:204273z, 15 pp., "A Method of Evaluating Irritation by Surfactants Using Liposomes", Takamura et al., Meiji Yakka Diagku Kenkyu Kiyo, vol. 12, pp. 7–15 (1982).

Chemical Abstract No. 100:63563q of "Effect of Amphosphilic Detergents on Liposome Membranes", J. Kuczera, 1983.

Chemical Abstract No. 98:27916p of "Action of Drugs, Detergents and Monomers on Liposomes", J. Dent. Res., vol. 61(10), pp. 1206–1210, 1982.

Chemical Abstract No. 100:2443d of "Detergent Effects on Enzyme Activity and Solubilization of Lipid Bilayer Membrances", M. Womack et al., Biochim. Biophys. Acta., vol. 733(2), pp. 210–215, 1983.

"The Application of Liposomes to Cosmetics", Suzuki et al., Cosmetics & Toiletries, vol. 105, May 1990, pp. 65ff.

"Liposomes in Dermatological Preparations Part I", Lautenschlager, Cosmetics & Toiletries, vol. 105, May 1990, pp. 89ff.

"Liposomes in Dermatological Preparations Part II", Lautenschlager, Cosmetics & Toiletries, vol. 105, Jul. 1990, pp. 63ff.

"Liposomal Cosmetics", Wendel et al., Soap/Cosmetics/Chemical Specialties for Jun. 1990, pp. 32ff.

"Dispersions of Lamellar Phases of Non-ionic Lipids in Cosmetic Products", Handajani-Vila et al., Intl. J. of Cos. Sci., vol. 1, 1979, pp. 303–314.

"Liposomes: From theoretical model to cosmetic tool", Strauss, J. Soc. Cosmet. Chem., vol. 40, Jan./Feb. 1989, pp. 51–60.

"Synthetic Bilayer Membranes with Anionic Head Groups", Kunitake et al., Bulletin of the Chemical Society of Japan, vol. 51, No. 6, 1978, pp. 1877ff.

"Neutron Small Angle Scattering of Liposomes in the Presence of Detergents", Nawroth et al., Physica B 156 & 157, 1989, pp. 477–480.

"A Comparison of TRITON X-100 and the Bile Salt Taurocholate as Micellar Ionphores or Fusogens in Phospholipid Vesicular Membranes", G. Hunt, FEBS Letters, vol. 119, No. 1, Sep. 1980, pp. 132–136.

"Interaction of Surface Active Agents with Lecithin at the Xylene/Water Interface and its Effect on the Stability of the Resulting Emulsion", Sabet et al., Colloids and Surfaces, vol. 4, 1982, pp. 359–366.

"Interaction of an Amphoteric Surfactant with Lecithin at the Air/Water and Oil/Water Interfaces and its Effect on Emulsion Stability", Zourab et al., J. Disp. Sci. and Technol., 5(1), 1984, pp. 61–71.

"The Thermodynamical and Mechnical Condition of the Stable, Single Bilayer Vesicles as a Micellar Form of Surfactants", Suezaki et al., J. Coll. and Interf. Sci., vol. 114, No. 1, Nov. 1986, pp. 131–139.

"Spontaneous Vescile Formation in Aqueous Mixtures of Single-Tailed Surfactants", Kaler et al., Science, vol. 245, Sep. 1989, pp. 1371–1374.

Abstract of PCT WO 90/06106 from Word Patents Index on Dialog Information Services, Printout dated Dec. 14, 1990, 2 pgs.

"Application of Soy Phospholipid Liposomes in Cosmetic Products", Lautenschlager et al., Siefen-Oele-Fette-Wachse, vol. 114(14), 1988, pp. 531–534, 7 page English translation of German article.

"Detergent Effects on Enzyme Activity and Solubilization of Lipid Bilayer Membranes", M. Womack et al., Biochimica et Biophysica Acta, vol. 73, pp. 210–215 (1983).

"Action of Drugs, Detergents and Monomers on Liposomes", S. Fujisawa et al., Journal of Dental Research, vol. 61, No. 10, pp. 1206–1210 (Oct. 1982).

Translation, "Effect of Amphiphilic Detergents on Liposome Membranes", J. Kuczera, Problems of Contemporary Biophysics, pp. 53–101, (1983), translated from Polish Language, 67 pages total.

*McCutcheon's Detergents & Emusifiers,* 1973 No. American Edition, McCutcheon's Division, Allured Publ. Corp., Ridgewood, N.J., (1973), pp. 4, 16, 46 & 84.

DETERGENT COMPOSITIONS CONTAINING LIPOSOMES AND PROCESS THEREFOR

This is a divisional of co-pending application Ser. No. 07/578,913 filed on Sep. 6, 1990, now abandoned.

TECHNICAL FIELD

This invention relates to a method of stabilizing liposomes contained in aqueous compositions against lysis by anionic surfactants otherwise known to disrupt and lyse such liposomes by using certain surfactants as stabilizing agents and to the stabilized compositions obtained thereby as well as to a method of making detergent compositions containing such stabilized liposomes and anionic surfactants and to the compositions themselves.

BACKGROUND ART

The patent and journal literature is replete with information concerning "liposomes" which term, as used herein, will mean bilayer vesicles derived from amphiphilic molecules which are either anionic or nonionic in charge. The liposomes can be unilamellar or multilamellar. Thus, "liposomes" can include vesicles derived from natural phospholipids as well as those from synthetic nonionic amphiphilic compounds which are sometimes called "niosomes".

The cosmetic use of such materials is rapidly gaining importance in the cosmetic marketplace. Recent summaries of information concerning liposomes include two articles in the May, 1990 issue of *Cosmetics & Toiletries*, Vol. 105: "The Application of Liposomes to Cosmetics" by Suzuki et al. on page 65ff and "Liposomes in Dermatological Preparations Part I" by Lautenschlager on page 89ff, an article in the July, 1990 issue of *Cosmetics & Toiletries:* "Liposomes In Dermatological Preparations Part II" by Lautenschlager on page 63ff ("Lautenschlager II"), as well as in the June, 1990 issue of *Soap/Cosmetics/Chemical Specialties:* "Liposomal Cosmetics" by Wendel et al. on page 32ff, the 1979 issue of *International Journal of Cosmetic Science*, Vol. 1: "Dispersions of lamellar phases of non-ionic lipids in cosmetic products" by Handajani-Vila et al. on page 303ff, and the January/February, 1989 issue of *Journal of the Society of Cosmetic Chemists*, vol. 40: "Liposomes: From theoretical model to cosmetic tool" by Strauss. The Strauss article notes that liposomes can encapsulate water-soluble cosmetics in their aqueous compartments. It states that detergents and surfactants are added, but are later removed by dialysis or gel filtration to form the liposomes (FIG. 2) while page 56 states that surfactants can be encapsulated in liposomes. Other examples of liposome preparation are found in U.S. Pat. Nos. 4,438,052 to Weder et al., 4,536,324 to Fujiwara et al. (nonionic liposomes), 4,708,861 to Popescu et al., 4,853,228 to Wallach et al. (nonionic liposomes—charged surfactants can be added to alter the ionic nature of the liposome formed), and 4,911,928 to Wallach et al. and the *Bulletin of the Chemical Society of Japan,* "Synthetic Bilayer Membranes with Anionic Head Groups", Kunitake et al., Vol. 51, No. 6, page 1877ff, 1978 (liposomes from synthetic anionic surfactants).

For cosmetic uses, liposome-containing formulations are generally in the form of lotions or creams which provide a vehicle which retains the bilayer structure of the liposomes. Liposomes, particularly those derived from phospholipids such as lecithin, are sensitive to other compounds which can lyse the bilayer forming the liposome particles. Lysis eliminates the presence of the vesicles comprising the liposomes and any cosmetic material such as a humectant carried within the aqueous interior compartment of the liposome is released into the surrounding aqueous media.

Skin creams and lotions are generally left on the skin or hair and are not rinsed off. It would be of significant cosmetic importance if liposomes could be included in products such as shower gels and hair shampoos. These products would both cleanse the body and impart the beneficial properties of liposomes to the skin and hair even though a shower gel or hair shampoo is normally rinsed away. Although the literature is somewhat contradictory on this point, anionic surfactants of the type typically used in shower gels and shampoos such as sodium laureth-2 sulfate act to lyse liposome vesicles. The liposomes are not stable in the presence of such surfactants and any beneficial effect they might have is reduced or eliminated by such lysis.

Liposome stability is particularly important when the liposomes are used to deliver an active ingredient such as a moisturizer or vitamin. For example, page 36 of the Wendel et al. article, supra, states "liposomal liquid soaps or shampoos generally cannot be formulated" in referring to natural phospholipid-derived liposomes. Wendel et al. further teach that liposomes are "quite stable in products with amphiphilic surfactants such as ethanol or ethylene glycol". U.S. Pat. No. 4,752,572 to Sundberg et al. teaches that liposomes are lysed by the addition of a surfactant with a critical micelle concentration of at least 0.1 millimole and states that examples of anionic surfactants used to lyse liposomes are sodium cholate and sodium dodecyl sulfate. Page 66 of the Lautenschlager II article states ". . . it is impossible to formulate liposomal liquid soaps or shampoos . . ." while page 70 refers to a stable oil-in-water cream containing liposomes as well as 0.5% polysorbate and 0.5% sorbitan mono-oleate as an example of a stable liposomal cream with very low proportions of emulsifiers.

U.S. Pat. No. 3,957,971 to Oleniacz teaches liposome suspensions containing entrapped humectants where the liposomes comprise a ternary mixture of lecithin, dicetyl phosphate and cholesterol and the humectant can be sodium pyroglutamate or glutamic acid. Contrary to other journal reports, Oleniacz teaches that such liposomes can be delivered from a vehicle containing anionic or amphoteric surfactants. Example 15 gives a shampoo formulation containing an anionic surfactant—triethanolammonium lauryl sulfate, ethanol, another surfactant—bis(2-hydroxyethyl)alkylamine oxide, ethanol and an aqueous composition containing liposomes in which sodium pyroglutamate was entrapped. The instructions state that the four ingredients are merely mixed together at room temperature while maintaining a pH of 5-6 until the solid components dissolve. Unlike Example 13 of Oleniacz where the stability of humectant-containing liposomes in the presence of 0.1 weight volume percent of various surfactants is reported, there is no indication that stable liposomes were present in the resulting shampoo composition. No specific order for mixing the ingredients together is given for Example 15.

In their article in *Physica B* 156 & 157 entitled "Neutron Small Angle Scattering of Liposomes in the Presence of Detergents" on page 477ff, Nawroth et al. conclude that small amounts of detergents such as bile salts (taurodexycholate sodium salt) can be incorporated into lecithin-based liposomes without destroying their structure. The liposomes were stabilized by the charged detergent. Nonionic detergents did not help to stabilize the liposomes while anionic and cationic detergents did. In this work, the detergents were incorporated into the liposomes during their formation.

Unlike the liposomes which are the subject of this invention, U.S. Pat. No. 4,885,159 to Miyake et al. teach a hair cosmetic which is a polymer vesicle obtained from the polymerization of a surfactant monomer vesicle having a quaternary ammonium cation and a polymerizable anion as a counterion. The products are said to be useful as a hair rinse to condition the hair. In addition to the polymeric vesicles, anionic surfactants can also be present.

SUMMARY DISCLOSURE OF THE INVENTION

It is one object of this invention to provide a simple means of stabilizing liposomes, particularly those derived from phospholipids and nonionic amphiphilic compounds, against the lysing effect of anionic surfactants. No special modification of the liposome bilayer by the addition of ingredients other than those commonly employed such as sterols is necessary.

Another object of the present invention is to provide aqueous liposome suspensions which further contain surfactants which do not cause appreciable lysis and breakdown of the liposomes and thereby enables the compositions to be used as shower gels, shampoos, detergents and the like for cleansing purposes. These compositions provide a vehicle for placing the liposomes in contact with the body, hair or other substrate. The liposomes themselves may further contain active ingredients such as water soluble humectants and vitamins which may be delivered to the skin and hair upon contact with the liposomes.

A still further object of this invention is to provide a detergent composition containing stabilized liposomes along with anionic surfactants of the type known to lyse liposomes such as sodium lauryl sulfate and sodium laureth sulfate which are commonly used in shower gels and shampoos. Use of such stabilized liposomes has the advantage of allowing formulators to use proven shower gel and shampoo formulations when products containing liposomes are desired.

These and other objects of the present invention are provided by a method of stabilizing an aqueous composition containing liposomes against the lysing effect of anionic surfactants which consists essentially of adding from about 0.1% to 40%, and more preferably, from 2% to 10%, by weight based upon the total weight of the composition of at least one surfactant selected from the group consisting of fatty alkyl sulfosuccinates where the fatty alkyl group contains from 8 to 22 carbons atoms, fatty acylamino polyglycol ether sulfates where the fatty acyl group contains from 8 to 22 carbon atoms, fatty alkyl amine oxides where the fatty alkyl group contains from 7 to 26 carbon atoms, fatty alkyl phosphate esters where the fatty alkyl group contains from 8 to 22 carbon atoms, and N-acyl amino acid salts or salts of N-acyl derivatives of hydrolyzed proteins of up to about 2,500 daltons in weight average molecular weight where the acyl portion is derived from a carboxylic acid having from 8 to 22 carbon atoms per molecule to an aqueous composition containing from about 0.1% to 50%, and more preferably from 5% to 30%, by volume of liposomes based upon the volume of the total composition, the amount of the surfactant present being such as to stabilize the liposomes against the effects of anionic lysing surfactants and, more preferably, where the ratio of the liposomes to the surfactant present is in a ratio of no greater than 30 parts by volume of liposomes to 1 part by weight of surfactant. References to amounts of "surfactants" herein and in the claims means the amount of active surfactant compound excluding inactive salts and water usually found in commercial surfactants. Preferably, the liposomes comprise phospholipids or amphiphilic nonionic compounds.

This invention further relates to a method involving adding to the aqueous composition containing liposomes described immediately above, from about 0.1 to 35%, and more preferably from 5% to 15%, by weight of the total detergent composition of at least one anionic surfactant which is known to lyse liposomes to form an aqueous detergent composition containing liposomes and such an anionic surfactant. Preferably, the anionic surfactant is selected from those of the formula $R^6(OCH_2CH_2)_gQ$ where $R^6$ is selected from the group consisting of alkyl groups of from 8 to 18 carbons atoms, phenyl groups, and alkaryl groups of from 6 to 24 carbon atoms, g has a value of from 0 to 10, and Q is selected from the group consisting of $-C(O)OZ$, $-OSO_3Z$ and $-SO_3Z$ and more preferably, sodium lauryl sulfate and sodium lauryl ether ("laureth") sulfate where g has an average value of from 1 to 10, and more preferably, from 1 to 4.

This invention also relates to the compositions obtained by the above methods.

BEST MODE OF CARRYING OUT THE INVENTION

Figure 1:
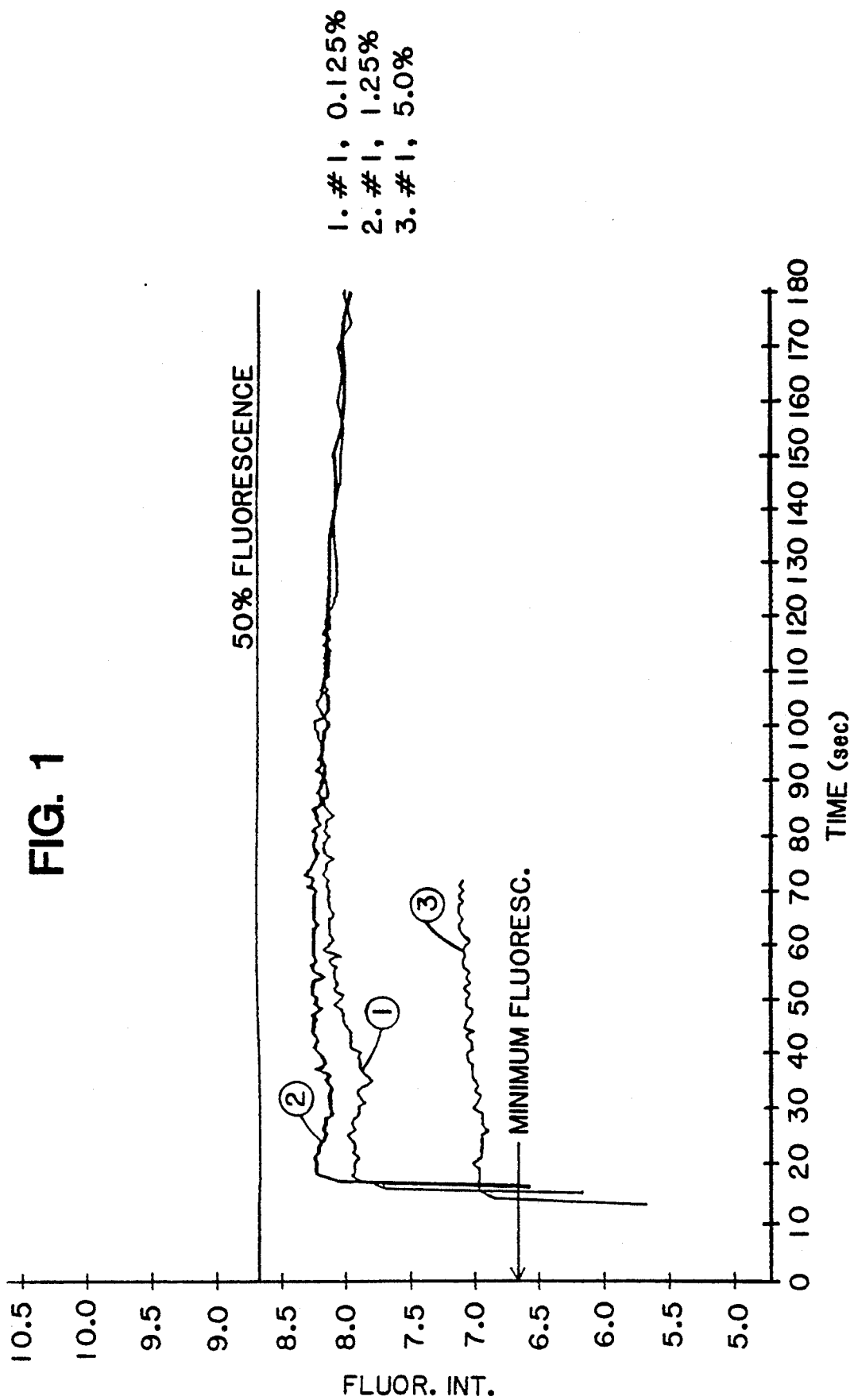
FIG. 1 is a visible light fluorimeter spectrograph ("Fluorimeter Spectrograph") taken after adding disodium laureth-3 sulfosuccinate to aqueous dye-containing phospholipid-based liposomes.

The techniques and materials used to prepare liposomes and to incorporate various ingredients therein are well known to those of ordinary skill in the art as exemplified by the journal articles and patents previously noted. The art recognizes various classes of liposomes. The nomenclature used to describe them can be confusing since liposomes can be described as a function of the number of bilayers present or as a function of the method of preparation. The following is an example of frequently used nomenclature:

| Type of Vesicle | Term | Average Diameter microns ($\mu$) |
|---|---|---|
| Small, Sonicated Unilamellar | SUV | 0.025–0.05 |
| Large Vortexed Multilamellar | MLV | 0.05–10 |
| Large Unilamellar | LUV | 0.1 |
| Reverse Phase Evaporation | REV | 0.5 |
| French Press | FPV | 0.05 |

The present invention relates to methods for stabilizing liposomes and the manner in which they are produced is not believed to be critical to this invention.

The liposomes used in the present invention can be based upon phospholipids which are sometimes called "lecithins". They are the esters of oleic, stearic, palmitic or other fatty acids with glycerophosphoric acid and choline. Lecithins can be obtained from both animal and vegetable tissues as well as from egg yolks. Specific examples of phospholipids (including the temperature at which the pure membranes melt or "$T_m$" in parentheses) which can be used to form liposomes are dioleoyl phosphatidylcholine (−22° C.), dilauryl phosphatidylcholine (0° C.), dimyristoyl phosphatidylcholine (23° C.), dipalmitoyl phosphatidylcholine (41° C.), distearoyl phosphatidylcholine (58° C.), dimyristoyl phosphatidylethanolamine (48° C.), dipalmitoyl phosphatidylethanolamine (60° C.), dioleoyl phosphatidylglycerol (−18° C.), dilauryl phosphatidylglycerol (4° C.), dimyristoyl phosphatidylglycerol (23° C.), dipalmitoyl phosphatidylglycerol (41° C.), distearoyl phosphatidylglycerol (55° C.), and dipalmitoyl phosphatidic acid (at pH 6:67° C. and at pH 9:58° C.).

Examples of nonionic amphiphilic compounds useful in making nonionic liposomes can be those from the class of alkyl polyglycerides such as polyglyceryl-6 distearate, polyglyceryl-3 hydroxy lauryl ether and polyglyceryl-2 lanolin ether.

The $T_m$ of the liposome material affects the leakage of entrapped actives (incorporated into the interior of the liposomes) into the external continuous aqueous phase. Liposomes are least leaky in the gel state (below $T_m$), more leaky in the liquid crystalline state (above $T_m$) and most leaky at the exact temperature of phase transition or melting (at $T_m$). Some literature reports state that REVs are leakier than MLVs and others state the opposite.

As is known in the art, compounds such as sterols like cholesterol can be included as part of the bilayer material used to form the liposomes. The sterol tends to act as a filler and stabilizes the liposome membranes to reduce leakage. Thus, a modifier such as a sterol can reduce exchange of the entrapped materials within the liposomes with the aqueous continuous phase in which they are suspended. A molar ratio of 50:50 is about the most stable, although a ratio of 70:10 to 70:35 phospholipid:sterol is a more preferred molar ratio with molar ratios of 70:10 to 70:20 being most preferred. The addition of charged compounds such as dicetyl phosphate into the bilayer material used to form the liposomes generally prevents the vesicles from collapsing. We have found that liposomes made from a mixture of egg lecithin, dicetyl phosphate and cholesterol in a molar ratio of 7:2:2 can be used to form LUV and MLV liposomes suitable for use in the present invention and, more preferably, a molar ratio of 7:2:1 to 7:2:3.5 is used.

The method of Schieren et al. as reported in *Biochim et Biophys. Acta*, vol. 542, pp. 137–153 (1978) was used to prepare the aqueous LUVs described in the Examples. The MLVs were made by a thin film hydration method as described by Kinsky in *Methods in Enzymology*, XXXII, Biomembranes, Part B, pp. 501–513 (1974). Other methods for making liposomes will be apparent to those of ordinary skill in the art. Likewise, other water soluble active ingredients such as vitamins, humectants, dyes, etc., can be entrapped within the liposomes when they are prepared or incorporated into the bilayer if they are oil soluble as is evident from the prior art. The aqueous liposome suspensions can contain from about 0.1% to about 50%, and more preferably, from 5% to 30%, by volume of liposomes based upon the total volume of the aqueous liposome suspension.

After the aqueous compositions containing liposomes are prepared, the following classes of surfactants are added to those compositions in amounts ranging from about 0.1% to 40%, and more preferably, from about 2% to 10%, by weight, based upon the total weight of the composition, of at least one of the following surfactants:

Fatty alkyl sulfosuccinates can be employed where the fatty alkyl group contains from 8 to 22 carbons atoms. Examples of such surfactants are those of the formulas

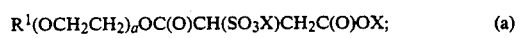

$R^1(OCH_2CH_2)_aOC(O)CH(SO_3X)CH_2C(O)OX;$ (a)

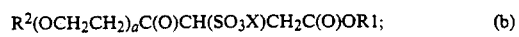

$R^2(OCH_2CH_2)_aC(O)CH(SO_3X)CH_2C(O)OR1;$ (b)

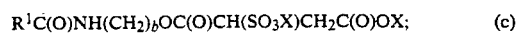

$R^1C(O)NH(CH_2)_bOC(O)CH(SO_3X)CH_2C(O)OX;$ (c)

and

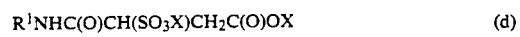

$R^1NHC(O)CH(SO_3X)CH_2C(O)OX$ (d)

wherein $R^1$ is an alkyl group having from 8 to 22 carbon atoms, $R^2$ is an alkyl group having from 4 to 16 carbon atoms, X is an anion such as an alkali metal such as sodium or potassium, sulfate, methylsulfate, ethylsulfate, ammonium, an amine of from 1 to about 9 carbon atoms such as methylamine, ethylamine, diethylamine and tri(n-propyl)amine or an alkanolamine of from about 2–9 carbon atoms such as monoethanolamine, diethanolamine, triethanolamine, and triisopropanolamine, a has a value of from 0 to 8, and b has a value of from 1 to 4.

Examples of such sulfosuccinates and formula (a) are disodium lauryl sulfosuccinate, disodium laureth-3 sulfosuccinate, disodium isodecyl sulfosuccinate, disodium deceth-6 sulfosuccinate, disodium stearyl sulfosuccinate, disodium cetearyl sulfosuccinate, disodium laueth-5 sulfosuccinate, and disodium laureth sulfosuccinate and dipotassium laureth sulfosuccinate where the average number of ethoxy groups present is between 1 and 4. Disodium laureth-3 sulfosuccinate and disodium laueth-5 sulfosuccinate were found to work well.

Examples of formula (b) are dioctyl sodium sulfosuccinate, dipalmityl sodium sulfosuccinate, and dilauryl potassium sulfosuccinate. Dioctyl sodium sulfosuccinate was found to work well.

Examples of formula (c) are disodium lauramido MEA sulfosuccinate; disodium cocamido MIPA-sulfosuccinate, disodium lauramido MEA-sulfosuccinate, disodium myristamido MEA-sulfosuccinate, disodium oleamido MEA-sulfosuccinate, disodium oleamido MIPA-sulfosuccinate, disodium stearamido MEA-sulfosuccinate, disodium undecylenamido MEA-sulfosuccinate, and dipotassium cocamido MIPA-sulfosuccinate.

Examples of formula (d) are disodium lauryl sulfosuccinamate, disodium oleyl sulfosuccinamate and tetrasodium dicarboxyethyl stearyl sulfosuccinamate.

Fatty acylamino polyglycol ether sulfates can be employed where the fatty acyl group contains from 8 to 22 carbon atoms. Examples of such surfactants are those of the formula:

$$R^3C(O)NH(CH_2CH_2O)_cSO_3X \quad \text{(e)}$$

wherein $R^3$ is an alkyl group having from 8 to 18 carbon atoms and c has a value of from 1 to 6.

Examples of formula (e) are TEA-PEG-3 cocamide sulfate, and sodium-PEG-5 stearamide sulfate.

Fatty alkyl amine oxides can be used where the fatty alkyl group contains from 7 to 26 carbon atoms. Examples of such surfactants are those of the formula:

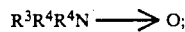  (f)

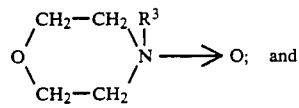  (g)

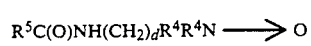  (h)

wherein $R^4$ is an alkyl group having from 1 to 4 carbon atoms or $-C_fH_{2f}OH$, $R^5$ is an alkyl group having from 7 to 26 carbon atoms, d has a value of from 1 to 5 and f has a value of 2 or 3.

Examples of formula (f) are cocamine oxide, lauramine oxide, myristamine oxide, stearamine oxide, laur(diethyl)amine oxide and behen(dimethyl)amine oxide.

Examples of formula (g) are coco-morpholine oxide, N-lauryl-morpholine oxide and N-stearyl-morpholine oxide.

Examples of formula (h) are cocamidopropylamine oxide, lauramidopropylamine oxide, caprylamidopropyl(diethyl) amine oxide, capramidoethyl(dimethyl)amine oxide, lauramidopropyl(diethyl)amine oxide and stearamidopropylamine oxide, and behenylamidopropyl(dimethyl)amine oxide.

Fatty alkyl phosphate esters can be used where the fatty alkyl group contains from 8 to 22 carbon atoms. Examples of such surfactants are those of the formula:

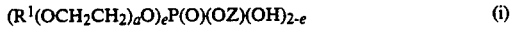  (i)

wherein Z is —H or X, and e has an average value of between 1 and 2.

Examples of formula (i) are sodium ceteareth-2 phosphate, DEA-oleth-1 phosphate, DEA-oleth-3 phosphate, sodium laureth-8 phosphate, sodium di(oleth-2) phosphate, sodium laureth-4 phosphate, potassium lauryl phosphate and sodium deceth-2 phosphate.

N-acyl amino acid salts, more preferably of aspartic acid or glutamic acid, or salts of N-acyl derivatives of hydrolyzed proteins of up to about 2,500 daltons in weight average molecular weight can be used where the acyl portion is derived from a carboxylic acid having from 8 to 22 carbon atoms per molecule.

Examples of such salts are sodium lauroyl glutamate, monotriethanolamine N-cocoyl-L-glutamate, sodium N-myristoyl-L-glutamate, potassium decoyl glutamate, sodium cocoyl glutamate, sodium stearoyl glutamate, potassium lauroyl aspartate, sodium stearoyl aspartate, sodium lauroyl aspartate, TEA-lauroyl glutamate, lauroyl-L-lysine, 2-octyldodecyl diester of N-lauroyl-L-glutamic acid, and potassium capryloyl aspartate.

Examples of such hydrolyzed proteins are potassium coco-hydrolyzed animal protein, TEA-coco-hydrolyzed animal protein, TEA-abietoyl hydrolyzed animal protein, TEA-lauroyl collagen amino acids, and potassium undecylenoyl hydrolyzed animal protein.

The stabilization of the liposome suspension, which may optionally contain entrapped and/or membrane incorporated (e.g., lipophilic materials may be carried by the lipid membrane rather than the aqueous interior of the liposomes) active ingredients such as vitamins, dyes, and humectants, among other things, is accomplished very simply by adding one or more of the above surfactants to the liposome suspension at room temperature with agitation. The composition can be agitated for a period of minutes to hours at room temperature after the addition is complete although the stabilization of the liposome suspension appears to occur very rapidly.

INDUSTRIAL APPLICABILITY

The stabilized liposome suspension can then be used as a shower gel, shampoo for the hair or detergent composition if a sufficient amount of the above surfactants are present to impart cleansing properties to the composition.

Other ingredients can be added to the composition provided that they are compatible with the liposomes present as can be discovered by simply adding the proposed ingredient to the stabilized liposome suspension. Thus, other ingredients such as dyes, thickening agents, preservatives, opacifiers, and the like can also be included in liposome suspensions stabilized by the method of the present invention.

The stabilized liposome suspensions can also be utilized as an added ingredient to shampoo and shower gel formulations which contain anionic surfactants which would otherwise disrupt the integrity of the bilayer walls of the liposomes present in the compositions and lyse them to destroy their vesicle nature. These types of anionic surfactants generally fall within the class of anionic surfactants which are readily commercially available and have been widely used in shampoos and shower gel formulations as well as for detergents for other purposes.

Examples of such anionic surfactants are those of the formula $R^6(OCH_2CH_2)_gQ$ as described previously which include surfactants such as sodium lauryl sulfate, ammonium lauryl sulfate, sodium laureth-2 sulfate, sodium cocoyl sulfate, sodium stearyl sulfate, sodium myristeth-4 sulfate and the like. Of these, the commercially important surfactants are sodium lauryl sulfate and sodium laureth sulfate where g has an average value of from 1 to 10, and more preferably, from 1 to 4 are preferred.

Other such anionic surfactants of the above formula can include linear alkyl benzenesulfonates where the alkyl group is octyl, dodecyl, tetradecyl, hexadecyl or octadecyl such as sodium dodecyl benzenesulfonate. Still other such anionic surfactants are $C_8$–$C_{25}$ olefin sulfonates such as sodium $C_{14}$–$C_{16}$ olefin sulfonate and sodium $C_{16}$–$C_{18}$ olefin sulfonate; $C_{10}$–$C_{20}$ paraffin sulfonates, such as those having from about 10 to 20, preferably from 10 to 15, carbon atoms such as the primary paraffin sulfonates made by reacting long chain alpha olefins and bisulfites (e.g., sodium bisulfite) or paraffin sulfonates having the sulfonate groups distributed along the paraffin chain such as the products made by reacting a long chain paraffin with sulfur dioxide and oxygen with ultraviolet light followed by neutralization with sodium hydroxide or other suitable base to provide an anion as a counterion; and $C_8$–$C_9$ alkyl phenyl ethoxamer sulfates such as sodium nonoxynol-4 sulfate, sodium octoxynol-2 ethane sulfonate, and ammonium nonoxynol-4 sulfate.

One or more of these lysing anionic surfactants can be employed in the method of the present invention by adding from about 0.1 to 35%, and more preferably from 5% to 15%, by weight of the total detergent composition of the anionic surfactant or surfactants to the stabilized liposome suspensions previously prepared. The addition of surfactant to the stabilized liposome suspensions is made with agitation and can be done at room temperature with agitation maintained until the resulting detergent composition is homogeneous. The result of the method is a detergent composition which can be used as a shower gel, hair shampoo or other detergent composition.

As will be appreciated by those of ordinary skill in the art, the final compositions should contain a sufficient level of liposomes to impart a beneficial effect to the body or hair if such contact is contemplated as a use for the composition.

The following Examples are provided to show various aspects of the present invention without departing from the scope and spirit of the invention. Unless otherwise indicated, all parts and percentages used in the Examples are by weight. In the following Examples, the methods and tests used were as follows:

Production of LUVs: Two different types of liposomes containing 5(6)-carboxyfluorescein as a dye-marker were produced by a modification of the method of Schieren et al. noted above. One type employed egg lecithin as the major anionic lipid compound: egg phosphatidyl choline (from frozen egg yolk):dicetyl phosphate:cholesterol in a 7:2:2 molar ratio (hereinafter referred to as "LUV-EPCs"). The other type of LUV employed a major amount of a nonionic amphiphilic compound: polyglyceryl-6 distearate (6G-2-S from Capital City Products Company):dicetyl phosphate:cholesterol in a 7:2:2 molar ratio (hereinafter referred to as "LUV-PGDs").

The membrane components (egg phosphatidyl choline (59.61 milligrams—"mg") or polyglyceryl-6 distearate:dicetyl phosphate (11.85 mg):cholesterol (7.14 mg) in a 7:2:2 molar ratio) were dissolved in about 25 milliliters (ml) of chloroform with the addition of a minimal amount of methanol (i.e., an amount sufficient to dissolve the dicetyl phosphate: about 2 ml) and, under reduced pressure, dried at 45° C. for at least two hours. The resulting dried film was then dissolved in 35 ml of petroleum ether (boiling range of 35° to 60° C.), the solution was divided in half and each half was taken up into a gas tight syringe. Each syringe was placed into a syringe pump and each solvent mixture was injected at between 0.1 and 0.2 ml per minute into one of two water-jacketed vessels containing 4 ml of a trapping solution which was an aqueous 0.05 Molar tris(hydroxymethyl) aminomethane ("TRIS") solution of pH 7.4 containing 0.01 Molar 5(6)-carboxyfluorescein wherein the solution was adjusted to 290 mOsm/kg $H_2O$ using sodium chloride before use. The trapping solution was kept at or above the boiling point of the solvent (60° C.). After completion of the injection, the liposome suspension was vortexed for one minute and allowed to cool to room temperature (about 22° C.). The untrapped dye was removed by gel chromatography by passing the suspension through a SEPHADEX G25 column.

Production of MLVs: These liposomes containing 5(6)-carboxyfluorescein were used in Examples 22–24. These liposomes employed distearyl phosphatidyl choline as the major anionic lipid compound: distearyl phosphatidyl choline (25 mg):dicetyl phosphate (4.92 mg):cholesterol (2.97 mg) in a 7:2:2 weight ratio (hereinafter referred to as "MLV-DPCs"). MLV-DPCs were produced by a thin film method as follows:

The preparation method used was initially the same as that used for the LUV-EPCs in that the membrane components were dissolved in chloroform with a minimal amount of methanol and were dried at 45° C. for 2 hours to produce a dried film. A special trapping solution was used to obtain better microphotographs: 50 grams of glucose was added to 100 ml of an aqueous buffer solution of pH 7.4 containing 0.01 Molar 5(6)-carboxyfluorescein and 0.05 Molar TRIS. Three milliliters of this trapping solution was added per 25 milligrams of distearyl phosphatidyl choline to the evaporation flask. The flask was heated in a water bath to 60° C. and the contents was agitated by gently swirling it. After the dried film was been hydrated, a creamy suspension was noted and the contents were agitated more vigorously for 15 minutes. The resulting liposome suspension was then cooled to room temperature and used in the following Examples without further processing.

Fluorimeter Spectrographs: To determine the stability of aqueous liposome suspensions, a water soluble dye which does not become incorporated into the liposome bilayer—5(6)-carboxyfluorescein from Eastman Kodak Company—was encapsulated within the aqueous interior of the liposomes to serve as a marker. This method for determining the integrity of a liposome suspension has been discussed in the literature in an article by Ralston et al. in *Biochim. Biophys. Acta,* Vol. 649, pp 133-137 (1981). The excitation and emission wavelengths for 5(6)-carboxyfluorescein are 492 nanometers (nm) and 520 nm, respectively.

Figure 2:
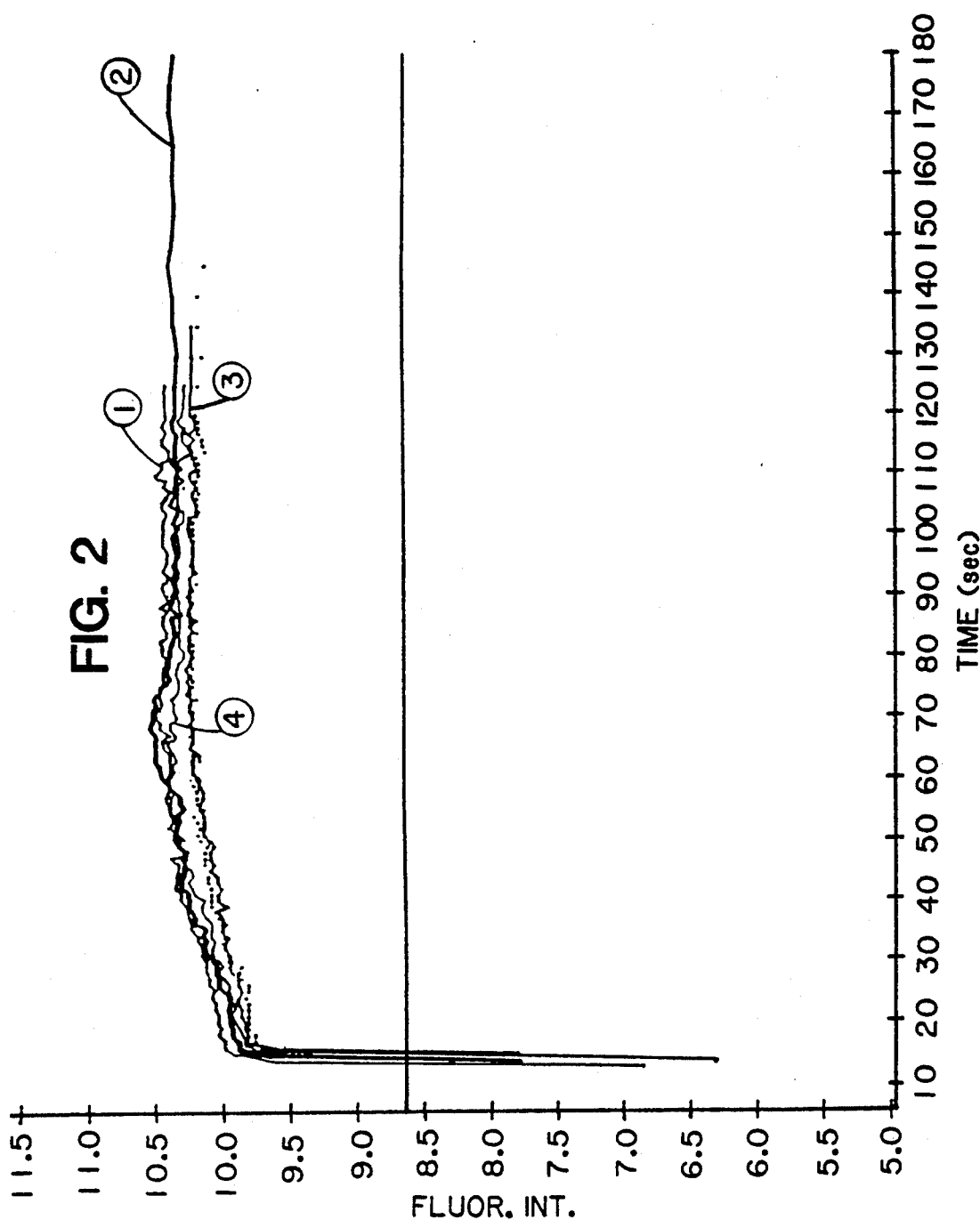
FIG. 2 is a Fluorimeter Spectrograph taken after adding an anionic surfactant, an alpha olefin sulfonate, known to lyse liposomes to aqueous dye-containing phospholipid-based liposomes.

To obtain the Fluorimeter Spectrographs of the type shown as FIGS. 1 and 2, the Fluorescent Intensity of a liposome suspension was measured at 520 nm using a Perkin Elmer 650S Fluorescence Detector which was interfaced with an IBM Personal computer to generate a Fluorimeter Spectrograph covering an arbitrary time period until no further significant increase in fluorescence was observed, typically a period of 150 to 180 seconds of time. Since the 5(6)-carboxyfluorescein is strongly pH dependent, any surfactants and buffers coming into contact with liposome suspensions were adjusted to pH 7.4. In addition, the osmolality of the solutions was adjusted to 290 mOsm/kg $H_2O$ to prevent changes of 5(6)-carboxyfluorescin concentrations due to osmotic activity of the liposomal membranes.

The maximum fluorescent intensity of a liposome suspension was determined by completely lysing a sample of the liposomes by introducing an aliquot (usually 25 microliters) of the liposome suspension containing entrapped dye into 4 ml of a 1% solution of sodium dodecyl sulfate. For liposomes based upon nonionic amphiphilic compounds, octoxynol-9 was used in place of the sodium dodecyl sulfate. To determine the minimum fluorescent intensity, an aliquot of liposome suspension of the same volume was added to 4 ml of isotonic buffer solution at pH 7.4. The 50% fluorescent intensity level indicated on the Fluorimeter Spectrographs was calculated as being the fluorescent intensity lying half way between the maximum and minimum fluorescent intensity values obtained for the liposome suspension.

Fluorimeter Spectrographs of liposome suspensions in the presence of specific surfactants were made by adding a 25 microliter aliquot of the dye-containing liposomes to be tested to 4 ml of the surfactant solution of the desired test concentration at room temperature (about 22° C.) and then immediately transferring it to a fluorimeter cuvette. All surfactant solutions were adjusted to be isotonic with sodium chloride and buffered with 0.05 Molar TRIS and adjusted to a pH of 7.4 with hydrochloric acid. Lysis of liposomes occurred very rapidly at room temperature. A liposome suspension was considered to be stable in the presence of a surfactant if the equilibrium reading (typically reached within 10-20 seconds and normally after 60 seconds after addition of the aliquot to the surfactant solution) of fluorescent intensity did not exceed the 50% fluorescent intensity level for the liposome suspension being used.

The spectrographs represent the development of fluorescent intensity over time. When initially prepared, each dye-containing liposome suspension possesses a certain intrinsic fluorescence which is the minimum fluorescent intensity. Upon addition of the liposomes to a surfactant solution which interacts with the liposome membrane without lysing it, a slight increase in the fluorescent intensity is almost always observed. This instant leakage of dye is well known to formulators of liposome preparations used for drug delivery. Such leakage was not deemed to be indicative of liposome lysis unless it exceeded the 50% fluorescent intensity described above. That level was set as an arbitrary maximum beyond which the surfactant-liposome interaction was deemed to be destructive. Compatibility of liposomes with surfactants tested is indicated by one or more of the following factors: fluorescence does not exceed the 50% fluorescent intensity at any useful surfactant concentration, decrease in levels of fluorescent intensity as the concentration of surfactant is increased, and development of fluorescence over time is negligible. FIG. 1 shows a Fluorimeter Spectrograph which exhibits all of these factors. During this work, the addition of surfactants generally led to a decrease in fluorescent intensity beyond the initial value. Such a decrease may be due to the binding of surfactant to the liposome membrane in such a way that the membrane becomes tighter and contracts, causing the elimination of water from the inside of the liposomes and consequently an increase in dye concentration and thus a reduction in fluorescent intensity because the dye quenches at higher concentrations.

In all of the following Examples, the surfactants used were industrial grade and no attempt was made to purify them.

EXAMPLES 1-3

Examples 1 and 2 illustrate the compatibility with LUV-EPCs of a fatty alkyl sulfosuccinate surfactant, disodium laureth-3 sulfosuccinate, as shown in FIG. 1 as compared with Example 3 where the lysing effect of an anionic surfactant, an alpha olefin sulfonate, is shown in FIG. 2.

In Example 1, LUV-EPCs were prepared as described above and aliquots were added to surfactant solutions containing 0.125%, 1.25% and 5.0%, respectively, of disodium laureth-3 sulfosuccinate obtained as SURFAGENE S30 from CHEM-Y, G.m.b.H. of West Germany with 40% active surfactant content, using the procedure described above under "Fluorimeter Spectrographs" and then Fluorimeter Spectrographs of each were immediately recorded. The results are shown in FIG. 1 where the minimum fluorescent intensity of the LUV-EPCs used prior to surfactant addition was found to be about 6.7 and the 50% fluorescent intensity was about 8.7. FIG. 1 shows that at a 0.125% active surfactant concentration, the equilibrium value of fluorescent intensity was about 8.1 after 60 seconds with about the same value for the 1.25% active surfactant concentration. At 5.0% active surfactant concentration, the fluorescent intensity rapidly reached an equilibrium value of about 7.1 after about 40 seconds. In all cases, the equilibrium value of each concentration of surfactant tested was less than the 50% fluorescent intensity value for the LUV-EPCs in the absence of the surfactants being tested and were thus stable in the presence of the disodium laureth-3 sulfosuccinate.

Example 2 was done in the same manner as Example 1 and used the same surfactant, but from a different manufacturer: disodium laureth-3 sulfosuccinate obtained as REWOPOL ® SBFA 30 from Rewo Chemische Werke G.m.b.H. of West Germany at 40% active surfactant content. The 50% fluorescent intensity value for the LUV-EPCs was about 8.7. The concentrations of disodium laureth-3 sulfosuccinate measured and their equilibrium fluorescent intensity after 60 seconds listed in parentheses were as follows: 0.125% (7.8); 1.25% (7.7); 3.75% (7.1) and 5.0% (6.7). This essentially confirms the results in Example 1 showing that the LUV-EPCs were stable in the presence of this surfactant.

Example 3 was done in the same manner as for Example 1 and Fluorimeter Spectrographs were recorded where the active levels of alpha olefin sulfonate anionic surfactant, sodium C14–C16 olefin sulfonate, obtained as ELFAN OS46 from Akzo Chemicals BV of the Netherlands at 37% active surfactant content, were 0.125%, 0.625%, 1.25% and 3.75%, respectively. In all surfactant levels tested, the anionic lysing surfactant used in this Example lysed a substantial amount of the liposomes present as shown in FIG. 2 by the fact that the equilibrium fluorescent intensity of each sample tested ranged between about 10.1 and 10.4 which is significantly greater than the 50% fluorescent intensity level of about 8.7. When other anionic surfactants of the type commonly used in shampoos and shower gels such as sodium lauryl sulfate, sodium laureth sulfate containing an average of from 0.5 to 8 ethylene oxide groups per molecule, and linear alkyl benzene sulfonate where the alkyl group contains about 12 carbon atoms are tested, results of the same type depicted in FIG. 2 are obtained.

Thus the LUV-EPCs were stable in the presence of the fatty alkyl sulfosuccinate surfactant, disodium laureth-3 sulfosuccinate, while the anionic alpha olefin sulfonate surfactant lysed a significant amount of the same type of untreated LUV-EPCs.

EXAMPLES 4–9

These Examples demonstrate the compatibility of LUV-EPCs with various classes of surfactants.

Example 4 was prepared in the same manner as Example 1 using a fatty acid alkylolamide sulfosuccinate, disodium lauramide MEA sulfosuccinate obtained as REWOPOL ® SBL 203 from Rewo Chemische Werke G.m.b.H. at 40% active surfactant content. The 50% fluorescent intensity value for the LUV-EPCs was about 8.7. The concentrations of active disodium lauramide MEA sulfosuccinate measured and their equilibrium fluorescent intensity after 60 seconds listed in parentheses were as follows: 0.125% (7.6); 1.25% (5.0); and 5.0% (4.5). This surfactant was compatible with the LUV-EPCs.

Figure 3:
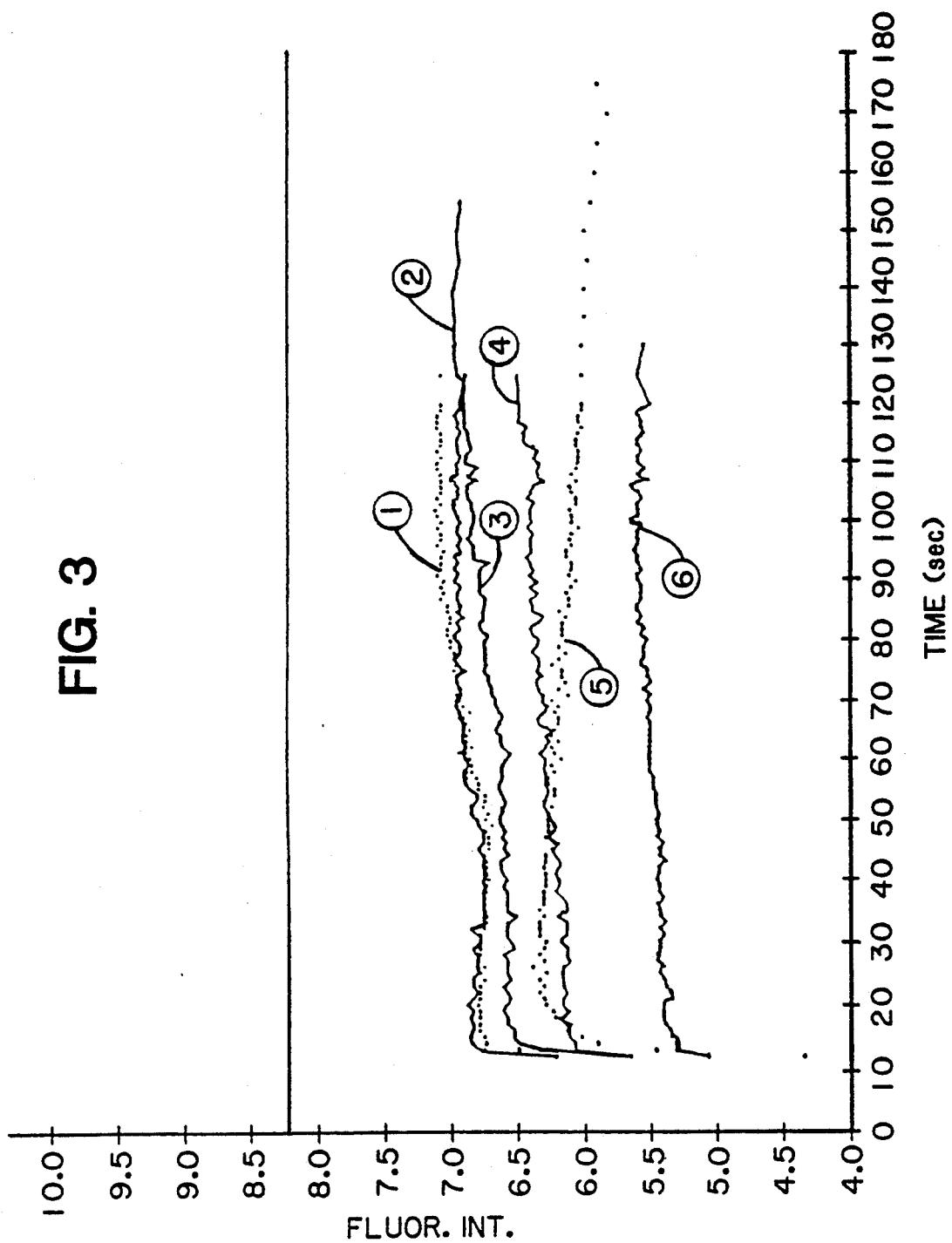
FIG. 3 is a Fluorimeter Spectrograph taken after adding sodium dioctyl sulfosuccinate to aqueous dye-containing phospholipid-based liposomes.

Example 5 was prepared in the same manner as Example 1 using a di-alkyl sulfosuccinate, sodium dioctyl sulfosuccinate, obtained as EMPIMIN OT from Albright & Wilson Ltd. of England at 60% active surfactant content. The 50% fluorescent intensity value for the LUV-EPCs was about 8.2 as shown in FIG. 3. The concentrations of active sodium dioctyl sulfosuccinate measured and their equilibrium fluorescent intensity after 60 seconds listed in parentheses were as follows: 0.092% (7.1); 0.125% (6.9); 0.185% (6.8); 0.462% (6.4); 2.78% (5.6) and 3.7% (6.0). This surfactant was compatible with the LUV-EPCs.

Example 6 was prepared in the same manner as Example 1 using a fatty acylamino polyglycol ether sulfate, TEA-PEG-3 cocamide sulfate obtained as GENAPOL ® AMS from Hoechst AG of West Germany at 40% active surfactant content. The 50% fluorescent intensity value for the LUV-EPCs was about 8.7. The concentrations of active TEA-PEG-3 cocamide sulfate measured and their equilibrium fluorescent intensity after 60 seconds listed in parentheses were as follows: 0.125% (8.2); 0.625% (8.3); 1.25% (8.0); 3.75% (7.3) and 5.0% (6.8). This surfactant was compatible with the LUV-EPCs.

Figure 4:
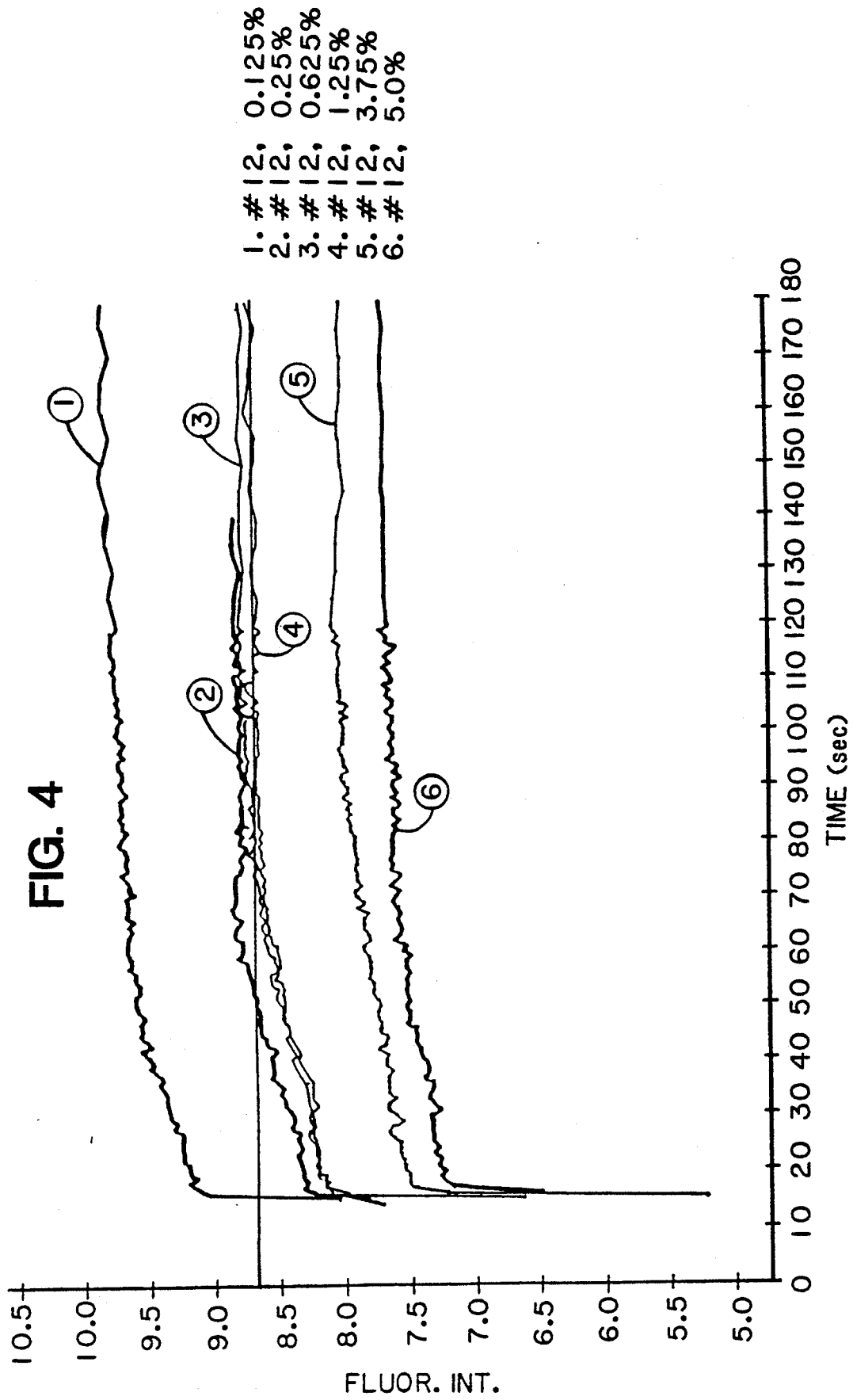
FIG. 4 is a Fluorimeter Spectrograph taken after adding cocamidopropylamine oxide to aqueous dye-containing phospholipid-based liposomes.

Example 7 was prepared in the same manner as Example 1 using a fatty alkyl amine oxide, cocamidopropylamine oxide, obtained as REWOMINOXID ® B204 from Rewo Chemische Werke G.m.b.H. at 35% active surfactant content. The 50% fluorescent intensity value for the LUV-EPCs was about 8.7 as can be seen in FIG. 4. The concentrations of active cocamidopropylamine oxide measured and their equilibrium fluorescent intensity after 60 seconds listed in parentheses were as follows: 0.125% (9.8); 0.25% (8.8); 0.625% (8.8); 1.25% (8.7); 3.75% (8.0) and 5.0% (7.6). This surfactant was not compatible with the LUV-EPCs at concentrations of up to about 1.25%, but quite unexpectedly, is compatible with the LUV-EPCs at higher concentrations. Thus to be effective as a stabilizer, this amine oxide must be used at concentrations in excess of 1.25%.

Example 8 was prepared in the same manner as Example 1 using an N-acyl amino acid salt, sodium lauroyl glutamate, obtained as AMISOFT ® LS-11 from Ajinomoto USA, Inc. of Teaneck, N.J. at 93% active surfactant content. The 50% fluorescent intensity value for the LUV-EPCs was about 8.7. The concentrations of active sodium lauroyl glutamate measured and their equilibrium fluorescent intensity after 60 seconds listed in parentheses were as follows: 0.125% (6.7); 1.25% (6.3); 3.75% (5.8) and 5.0% (6.1). This surfactant was compatible with the LUV-EPCs.

Example 9 was prepared in the same manner as Example 1 using a salt of an N-acyl derivative of hydrolyzed protein (i.e., the potassium salt of a fatty acid/protein condensate), potassium coco-hydrolyzed animal protein, obtained as REWOTEIN ® CPK from Rewo Chemische Werke G.m.b.H. at 25% active surfactant content. The 50% fluorescent intensity value for the LUV-EPCs was about 8.7. The concentrations of active potassium coco-hydrolyzed animal protein surfactant measured and their equilibrium fluorescent intensity after 60 seconds listed in parentheses were as follows: 0.086% (7.4); 0.43% (7.5); 0.86% (7.1); 2.59% (6.8) and 3.45% (6.6). This surfactant was compatible with the LUV-EPCs.

EXAMPLES 10–13

These Examples demonstrate the compatibility of nonionic LUV-PGDs with various classes of surfactants.

Figure 5:
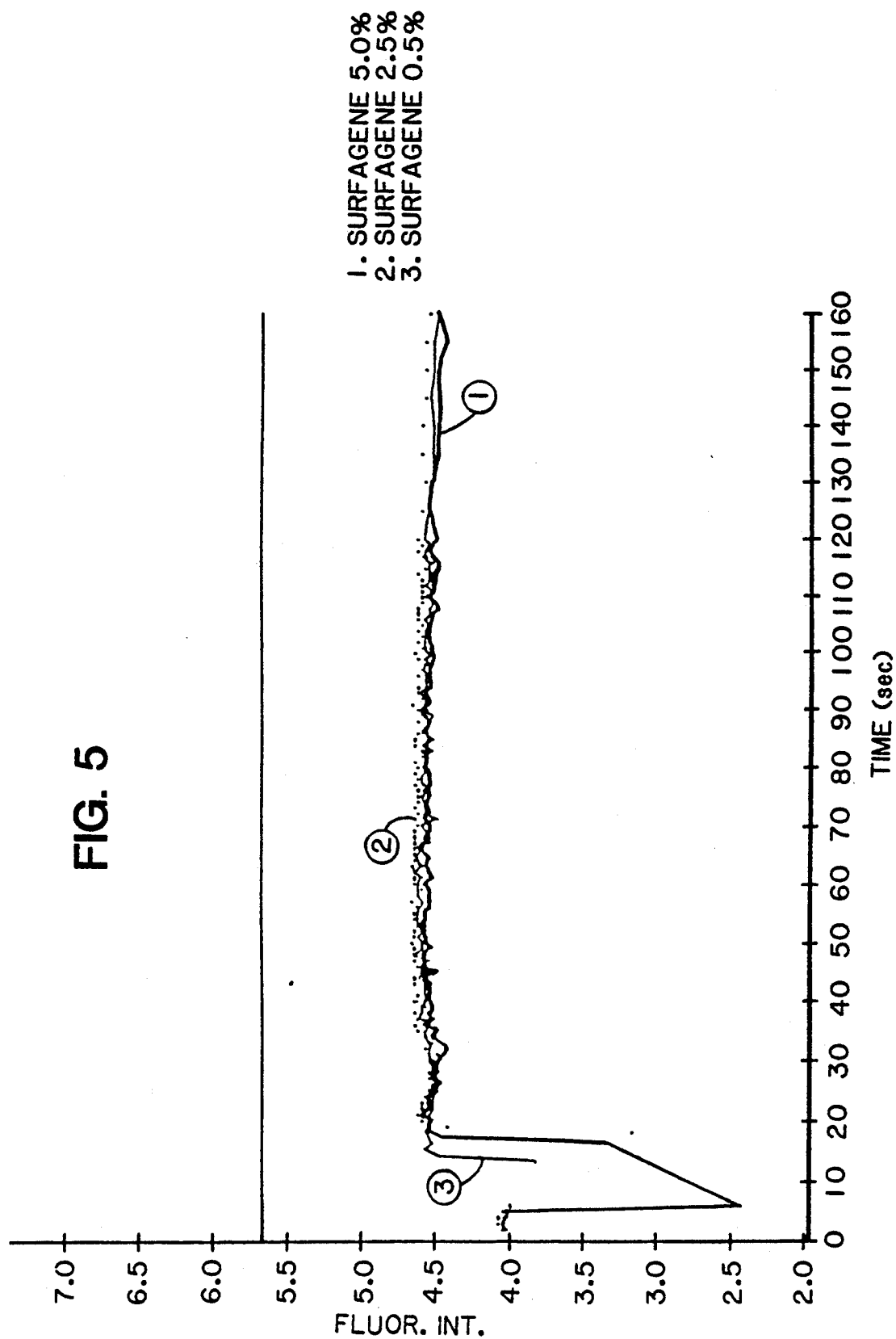
FIG. 5 is a Fluorimeter Spectrograph taken after adding disodium laureth-3 sulfosuccinate to aqueous dye-containing synthetic nonionic amphiphilic compound-based liposomes.

Example 10 was prepared in the same manner as Example 1 using the same surfactant, disodium laureth-3 sulfosuccinate obtained as SURFAGENE S30, but substituting LUV-PGDs for the LUV-EPCs used in Example 1. The 50% fluorescent intensity value for the LUV-PGDs was about 5.7 as can be seen in FIG. 5. The concentrations of active disodium laureth-3 sulfosuccinate surfactant measured and their equilibrium fluorescent intensity after 60 seconds listed in parentheses were as follows: 0.5% (4.6); 2.5% (4.6) and 5.0% (4.5). This surfactant was compatible with the LUV-PGDs.

Example 11 was prepared in the same manner as Example 9, but LUV-PGDs were substituted in place of the LUV-EPCs used in Example 9. The 50% fluorescent intensity value for the LUV-PGDs was about 5.7. The concentrations of active potassium salt of a fatty acid/protein condensate surfactant measured and their equilibrium fluorescent intensity after 60 seconds listed in parentheses were as follows: 0.345% (3.6); 1.725% (3.7) and 3.45% (4.1). This surfactant was compatible with the LUV-PGDs.

Example 12 was prepared in the same manner as Example 6, but LUV-PGDs were substituted in place of the LUV-EPCs used in Example 6. The 50% fluorescent intensity value for the LUV-PGDs was about 5.7. The concentrations of active TEA-PEG-3 cocamide sulfate surfactant measured and their equilibrium fluorescent intensity after 60 seconds listed in parentheses were as follows: 0.5% (4.5) and 5% (4.6). This surfactant was compatible with the LUV-PGDs.

Figure 6:
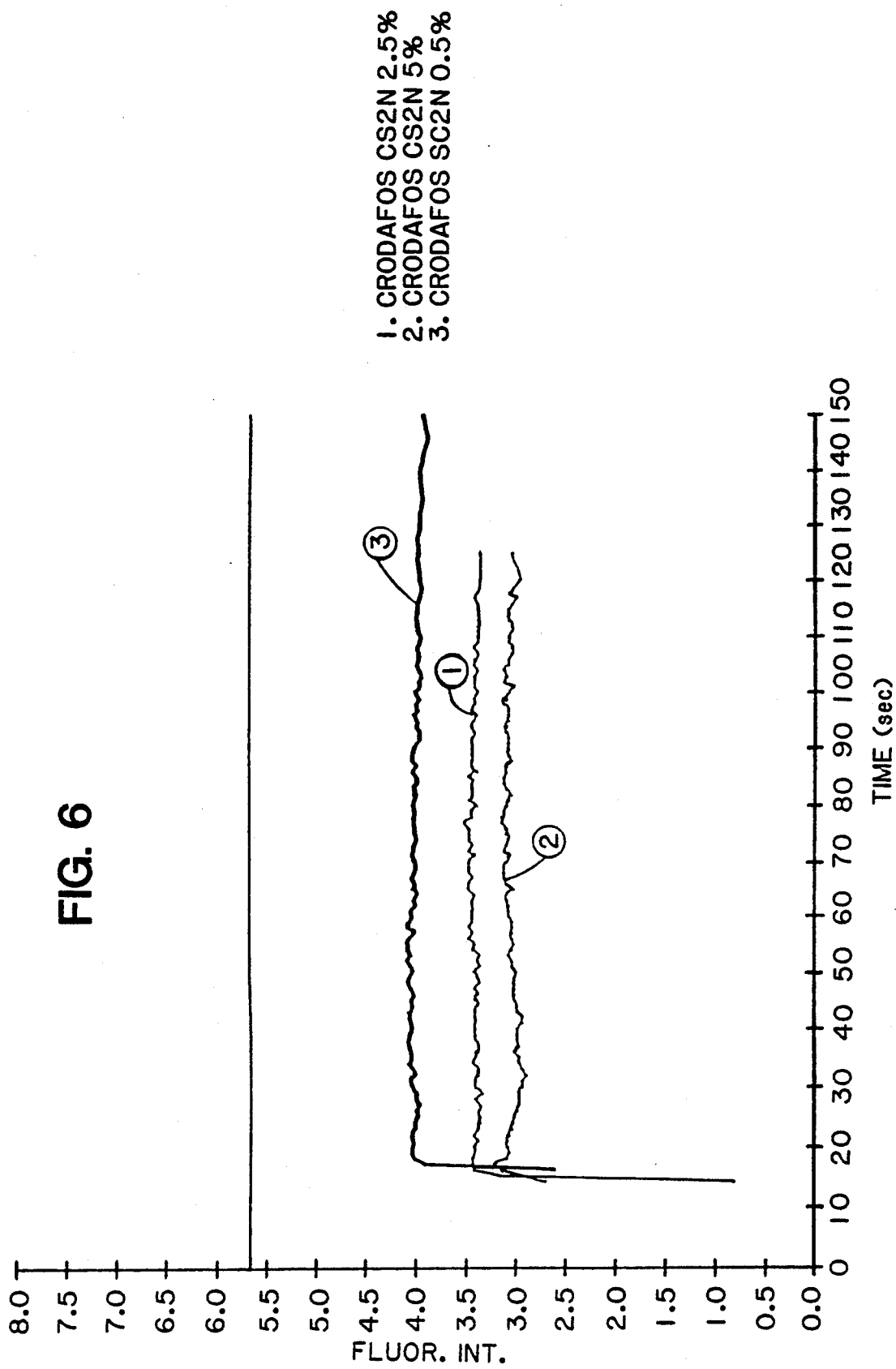
FIG. 6 is a Fluorimeter Spectrograph taken after adding sodium ceteareth-2 phosphate to aqueous dye-containing synthetic nonionic amphiphilic compound-based liposomes.

Example 13 was prepared in the same manner as Example 1, but LUV-PGDs were substituted in place of the LUV-EPCs used in Example 1 and the surfactant used was a fatty alkyl phosphate ester, sodium ceteareth-2 phosphate obtained as CRODAFOS CS2N from Croda Chemicals Ltd. of England at 99% active surfactant content. The 50% fluorescent intensity value for the LUV-PGDs was about 5.7 as shown in FIG. 6. The concentrations of active sodium ceteareth-2 phosphate surfactant measured and their equilibrium fluorescent intensity after 60 seconds listed in parentheses were as follows: 0.5% (4.0); 2.5% (3.4) and 5% (3.1). This surfactant was compatible with the LUV-PGDs.

EXAMPLES 14-18

In this series of Examples, the preparation of detergent compositions containing stabilized liposome suspensions of the present invention along with an anionic surfactant which typically lyses liposomes, sodium laureth-2 sulfate, was demonstrated along with data concerning the stability of the liposomes in such compositions.

Figure 7:
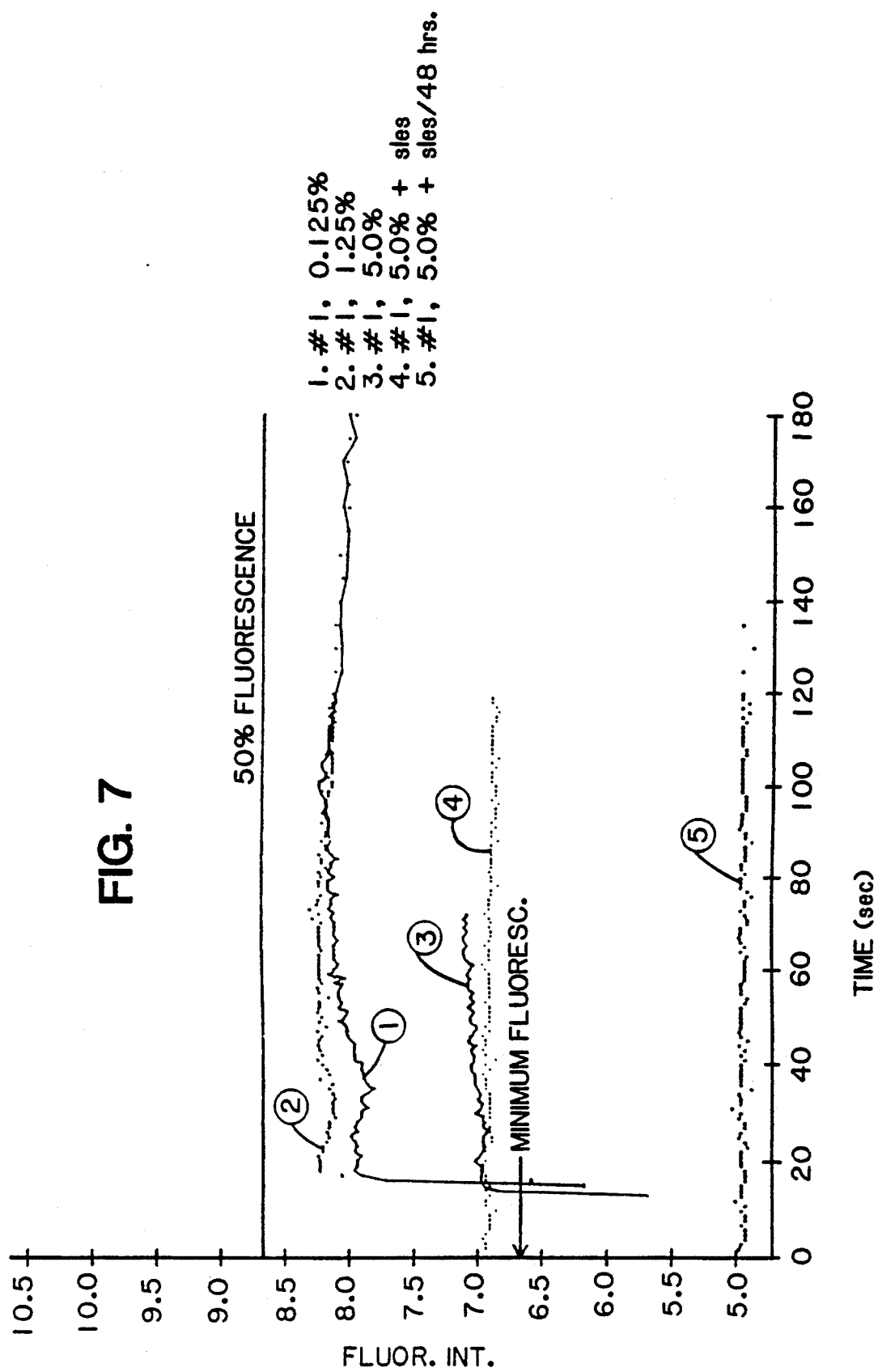
FIG. 7 is a Fluorimeter Spectrograph taken after adding sodium laureth-2 sulfate to aqueous dye-containing phospholipid-based liposomes stabilized with didodecyl sulfosuccinate to form a detergent composition.

In Example 14, LUV-EPCs were stabilized with various amounts of disodium laureth-3 sulfosuccinate (SURFAGENE S30) as described in Example 1. Fluorimeter Spectrographs of the stabilized compositions were prepared as in Example 1. The minimum fluorescent intensity of the LUV-EPCs was 6.7 and the 50% fluorescent intensity value for the LUV-EPCs was about 8.7 as shown in FIG. 7. The concentrations of active disodium laureth-3 sulfosuccinate surfactant measured and their equilibrium fluorescent intensity after 60 seconds listed in parentheses were as follows: 0.125% (8.1); 1.25% (8.1) and 5% (7.1). This surfactant was compatible with the LUV-EPCs.

Then, 4 ml of the above liposome suspension stabilized with 5% active disodium laureth-3 sulfosuccinate surfactant was then added to 1 ml of a solution containing 5% active sodium laureth-2 sulfate to obtain a detergent composition containing stabilized liposomes on which a Fluorimeter Spectrograph was run immediately after preparation to obtain an equilibrium fluorescent intensity of 6.8. The same detergent composition was then allowed to stand at room temperature (22° C.) for a period of 48 hours and the equilibrium fluorescent intensity was found to have decreased to 5.0 as shown in FIG. 7. This decrease in fluorescent intensity below the minimum fluorescence value for the LUV-EPCs was thought to possibly be due to the charge imparted to the liposomes imparted by the stabilization with sodium laureth-3 sulfosuccinate followed by the subsequent addition of excess electrolyte in the form of the sodium laureth-2 sulfate causing an overall reduction in free volume of the system. The unexpected result was that the liposomes were stabilized by the disodium laureth-3 sulfosuccinate so that they were then stable in the presence of the sodium laureth-2 sulfate which would otherwise be expected to lyse the liposomes and release the dye contained in them.

In Example 15, LUV-EPCs were stabilized with various amounts of disodium laureth-5 sulfosuccinate obtained as REWOPOL® SBFA50 from Rewo Chemische Werke G.m.b.H. at 40% active surfactant concentration as described in Example 14. Fluorimeter Spectrographs of the stabilized compositions were prepared as in Example 14. The 50% fluorescent intensity value for the LUV-EPCs was about 8.7. The concentrations of active disodium laureth-5 sulfosuccinate surfactant measured and their equilibrium fluorescent intensity after 60 seconds listed in parentheses were as follows: 0.125% (8.0); 1.25% (7.2); 3.75% (7.7) and 5% (7.4). This surfactant was compatible with the LUV-EPCs.

Then, 4 ml of the liposome suspension stabilized with 5% active disodium laureth-5 sulfosuccinate surfactant was then added to 1 ml of a solution containing 5% active sodium laureth-2 sulfate to obtain a detergent composition containing stabilized liposomes on which a Fluorimeter Spectrograph was run immediately after preparation to obtain an equilibrium fluorescent intensity of 7.3. The same detergent composition was then allowed to stand at room temperature (22° C.) for a period of 48 hours and the equilibrium fluorescent intensity was found to have decreased to less than 1.

Figure 8:
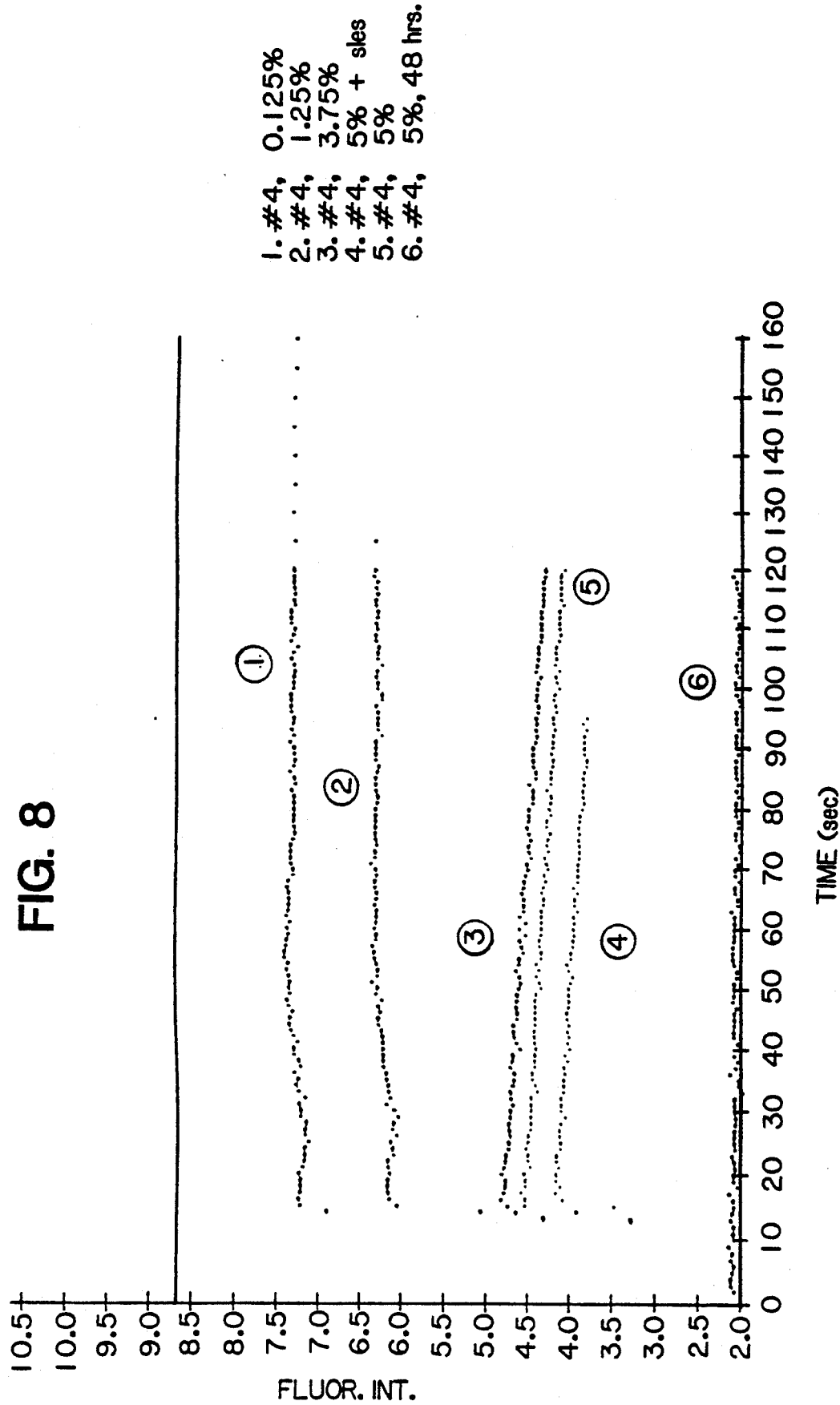
FIG. 8 is a Fluorimeter Spectrograph taken after adding sodium laureth-2 sulfate to aqueous dye-containing phospholipid-based liposomes stabilized with disodium laneth-5 sulfosuccinate to form a detergent composition.

In Example 16, LUV-EPCs were stabilized with various amounts of disodium laueth-5 sulfosuccinate obtained as REWOLAN® E from Rewo Chemische Werke G.m.b.H. at 50% active surfactant concentration as described in Example 14. Fluorimeter Spectrographs of the stabilized compositions were prepared as in Example 14. The 50% fluorescent intensity value for the LUV-EPCs was about 8.7 as shown in FIG. 8. The concentrations of active disodium laueth-5 sulfosuccinate surfactant measured and their equilibrium fluorescent intensity after 60 seconds listed in parentheses were as follows: 0.125% (7.4); 1.25% (6.3); 3.75% (4.4) and 5% (4.3). This surfactant was compatible with the LUV-EPCs.

Then, 4 ml of the liposome suspension stabilized with 5% active disodium laueth-5 sulfosuccinate surfactant was then added to 1 ml of a solution containing 5% active sodium laureth-2 sulfate to obtain a detergent composition containing stabilized liposomes on which a Fluorimeter Spectrograph was run immediately after preparation to obtain an equilibrium fluorescent intensity of 3.9. The same detergent composition was then allowed to stand at room temperature (22° C.) for a period of 48 hours and the equilibrium fluorescent intensity was found to have decreased to about 2.1.

In Example 17, LUV-EPCs were stabilized with various amounts of TEA-PEG-3 cocamide sulfate obtained as GENAPOL® AMS from Hoechst AG of West Germany at 40% active surfactant content as described in Example 6. Fluorimeter Spectrographs of the stabilized compositions were prepared as in Example 6. The 50% fluorescent intensity value for the LUV-EPCs was about 8.7. The concentrations of active TEA-PEG-3 cocamide sulfate surfactant measured and their equilibrium fluorescent intensity after 60 seconds listed in parentheses were as follows: 0.125% (8.2); 0.625% (8.3); 1.25% (8.0); 3.75% (7.3) and 5% (6.9). This confirms the results found in Example 6.

Then, 4 ml of the liposome suspension stabilized with 5% active TEA-PEG-3 cocamide sulfate surfactant was then added to 1 ml of a solution containing 5% active sodium laureth-2 sulfate to obtain a detergent composition containing stabilized liposomes on which a Fluorimeter Spectrograph was run immediately after preparation to obtain an equilibrium fluorescent intensity of 6.9. The same detergent composition was then allowed to stand at room temperature (22° C.) for a period of 72 hours and the equilibrium fluorescent intensity was found to have decreased to about 3.4.

Figure 9:
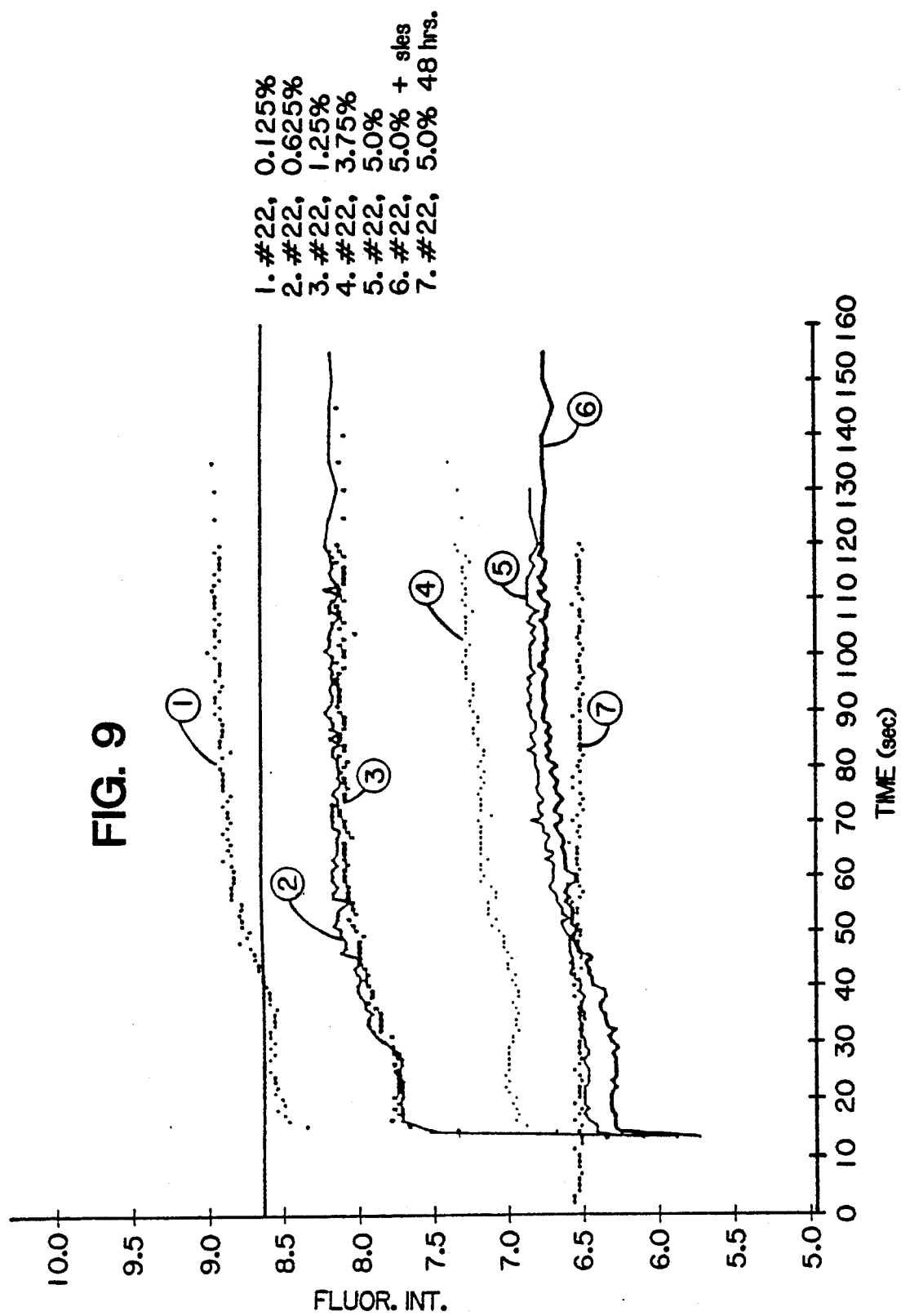
FIG. 9 is a Fluorimeter Spectrograph taken after adding sodium laureth-2 sulfate to aqueous dye-containing phospholipid-based liposomes stabilized with sodium ceteareth-2 phosphate to form a detergent composition.

In Example 18, LUV-EPCs were stabilized with various amounts of a fatty alkyl phosphate ester, sodium ceteareth-2 phosphate, obtained as CRODAFOS CS2N from Croda Chemicals Ltd. at 99% active surfactant content as described in Example 13, but LUV-EPCs were used in this Example 18. Fluorimeter Spectrographs of the stabilized compositions were prepared as in Example 13. The 50% fluorescent intensity value for the LUV-EPCs was about 8.7 as shown in FIG. 9. The concentrations of active sodium ceteareth-2 phosphate surfactant measured and their equilibrium fluorescent intensity after 60 seconds listed in parentheses were as follows: 0.125% (8.9); 0.625% (8.2); 1.25% (8.1); 3.75% (7.3) and 5% (6.8). This surfactant was not compatible with the LUV-EPCs at concentrations of up to about 0.125%, but quite unexpectedly, is compatible with the LUV-EPCs at higher concentrations. Thus to be effective as a stabilizer, this phosphate surfactant must be used at concentrations in excess of 0.125%.

Then, 4 ml of the liposome suspension stabilized with 5% active sodium ceteareth-2 phosphate surfactant was then added to 1 ml of a solution containing 5% active sodium laureth-2 sulfate to obtain a detergent composition containing stabilized liposomes on which a Fluorimeter Spectrograph was run immediately after preparation to obtain an equilibrium fluorescent intensity of 6.7. The same detergent composition was then allowed to stand at room temperature (22° C.) for a period of 48 hours and the equilibrium fluorescent intensity was found to have decreased to about 6.5.

EXAMPLES 19-21

In these Examples, detergent compositions containing LUV-PGDs stabilized with 5% disodium laureth-3 sulfosuccinate and each of three different anionic surfactants which typically lyse liposomes is illustrated as well as the stability of the stabilized LUV-PGDs in the presence of such anionic surfactants.

The stabilized liposome suspensions used in Examples 19-21 were made according to the same procedure described in Example 10 for the liposome suspensions stabilized with 5% of disodium laureth-3 sulfosuccinate (SURFAGENE S30). The LUV-PGDs were allowed to stabilize at room temperature for 30 minutes after the addition of the LUV-PGDs to the 5% disodium laureth-3 sulfosuccinate solution before the following compositions were made.

Figure 10:
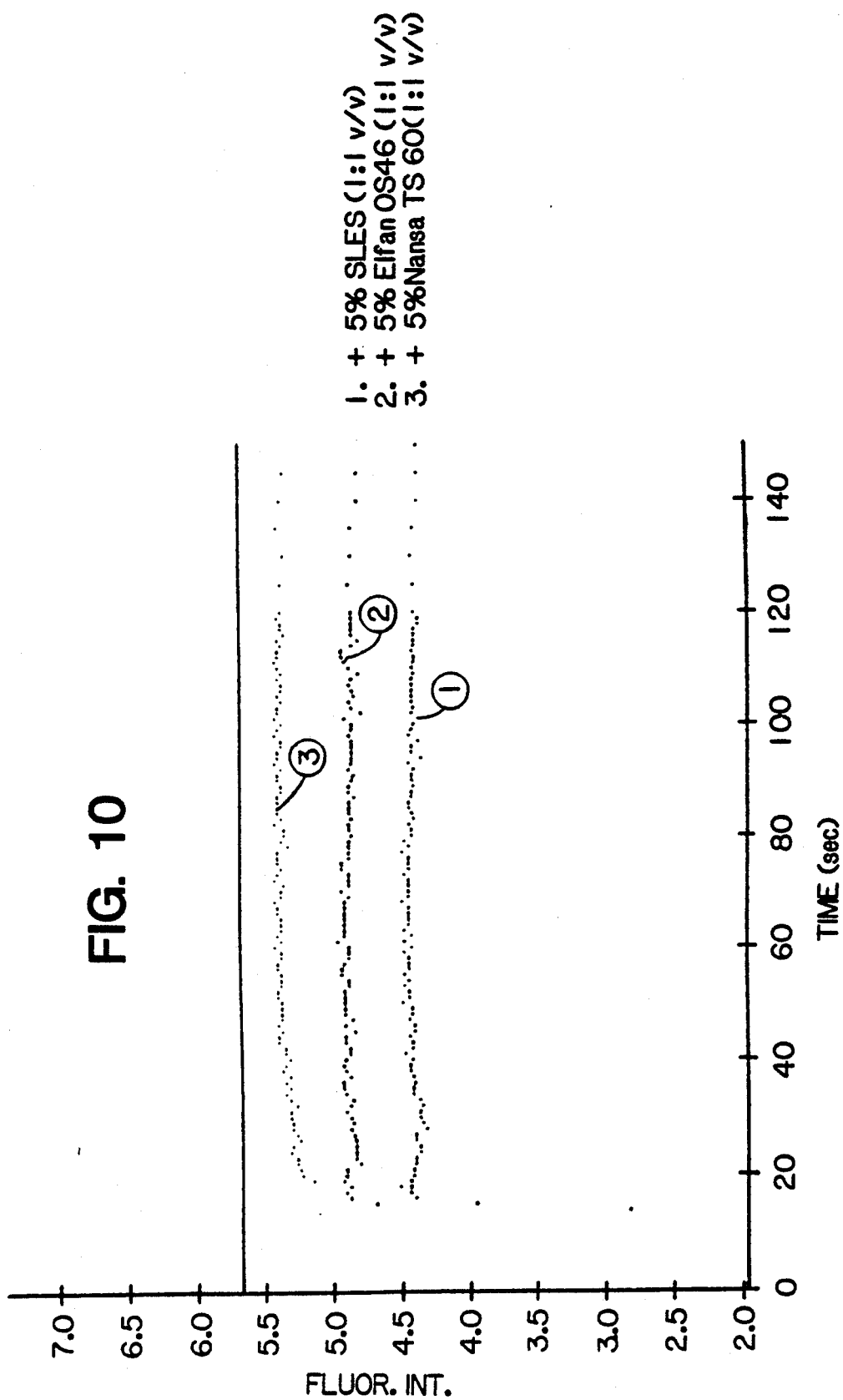
FIG. 10 is a Fluorimeter Spectrograph taken after adding several different anionic surfactants known to lyse liposomes to aqueous dye-containing synthetic nonionic amphiphilic compound-based liposomes stabilized with disodium laureth-3 sulfosuccinate.

Example 19 was prepared by adding the stabilized liposome suspension described above to a 5% buffered, isotonic aqueous solution of sodium laureth-2 sulfate on a 1:1 volume:volume basis and a Fluorimeter Spectrograph of the resulting detergent composition was made. As shown in FIG. 10, the 50% fluorescent intensity level of the LUV-PGDs was about 5.7 while the detergent composition of Example 19 had an equilibrium fluorescent intensity of 4.4 as shown in FIG. 10 indicating that the stabilized LUV-PGDs were stable in the presence of the sodium laureth-2 sulfate.

Example 20 was prepared in the same manner as was Example 19, but the anionic surfactant used was the alpha olefin sulfonate used in comparative Example 3, ELFAN OS46 from Akzo Chemicals BV. The detergent composition of Example 20 had an equilibrium fluorescent intensity of 4.8 as shown in FIG. 10 indicating that the stabilized LUV-PGDs were stable in the presence of the alpha olefin sulfonate.

Example 21 was prepared in the same manner as was Example 19, but the anionic surfactant used was a linear alkylbenzene sulfonate, TEA-dodecylbenzene sulfonate obtained as NANSA TS60 from Albright & Wilson Ltd. of England at 60% active surfactant content. The detergent composition of Example 21 had an equilibrium fluorescent intensity of 5.4 as shown in FIG. 10 indicating that the stabilized LUV-PGDs were stable in the presence of the TEA-dodecylbenzene sulfonate.

EXAMPLES 22-25

These Examples show facial wash detergent compositions including dye-containing stabilized liposome suspensions (MLV-DPCs). Example 24 further includes an anionic surfactant, sodium laureth-2 sulfate, known to lyse liposomes to show the stability of the MLV-DPCs in a detergent composition.

Figure 11:
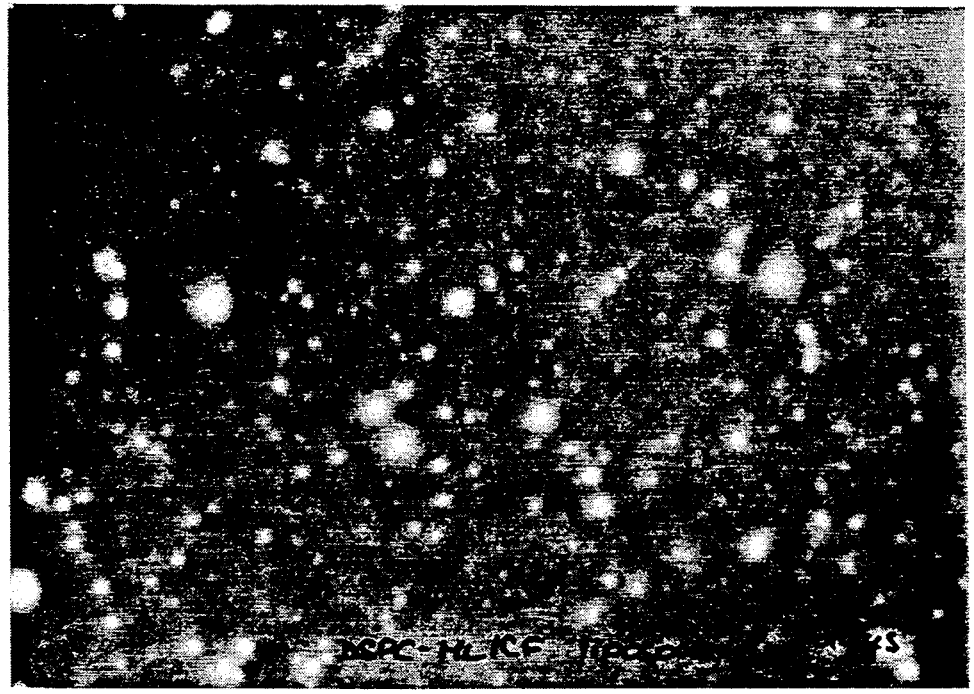
FIG. 11 is a 400× visible light microphotograph of aqueous dye-containing multilamellar liposomes in aqueous buffer solution taken 8 days after preparation.

FIG. 11 is a visible light microphotograph at 400 power magnification (400×) of the MLV-DPCs after treatment with a stabilizing amount (1.25%) of SURFAGENE S30 by adding 1 ml of 5% aqueous SURFAGENE S30 to 3 ml of the MLV-DPCs (hereinafter "Treated MLV-DPCs"). The bright spots in FIG. 11 represent liposome vesicles containing entrapped dye. The microphotographs included herein were time exposures made over a period exceeding one minute to capture enough light to register on the color photographic film and some blurring was observed due to the movement of the liposomes during the exposure period.

Figure 12:
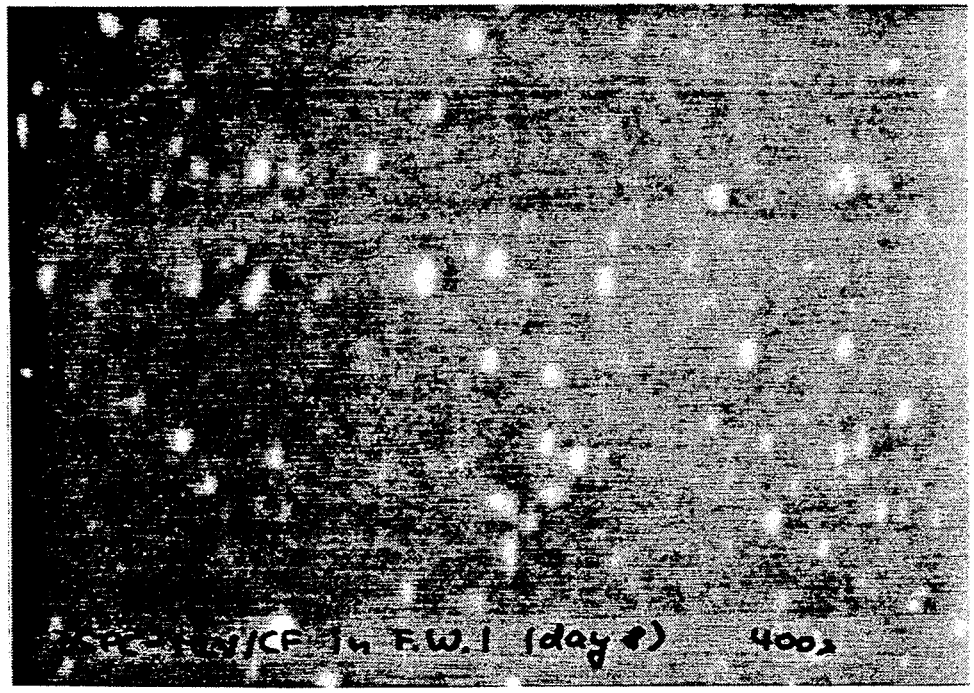
FIG. 12 is a 400× visible light microphotograph of aqueous dye-containing surfactant-treated multilamellar liposomes in detergent solution taken 8 days after preparation.

The detergent composition of Example 22 was made by adding 1.67 parts by volume of the Treated MLV-DPCs with stirring to 12.5 parts of SURFAGENE S30 (disodium laureth-3 sulfosuccinate) followed by 20 parts of GENAPOL ® AMS (TEA-PEG-3 cocamide sulfate) to obtain Example 22. That detergent composition was aged 8 days at room temperature and the 400× visible light microphotograph shown as FIG. 12 was taken as described for FIG. 11. FIG. 12 clearly shows the presence of vesicles containing dye and thus the liposomes were stable in this composition for that period of time.

In Examples 22-24, no additional water was added to the formulation and MLV-DPCs with sucrose were used (as described earlier) to obtain high viscosity compositions that would better show the presence of liposomes photographically since a relatively long exposure time was needed to obtain a microphotograph under 400× magnification. The formulations of Examples 22-24 were also prepared using MLVs which did not include sucrose. Each such formulation exhibited liposomes when diluted with deionized water to 100 ml volume. However, the liposomes tended to move in such aqueous detergent compositions to the extent that 400× magnification microphotographs taken with a time exposure registered a blurry microphotograph.

Figure 13:
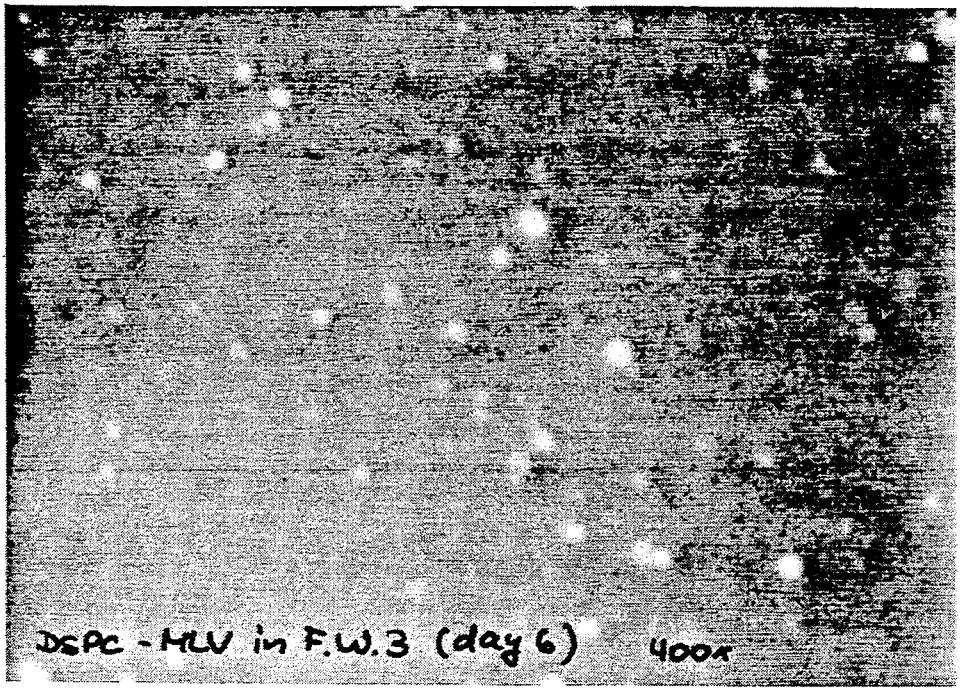
FIG. 13 is a 400× visible light microphotograph of aqueous dye-containing surfactant-treated multilamellar liposomes in detergent solution taken 6 days after preparation.

Example 23 was prepared in the same manner as Example 22 (additions made in the order listed), but had the following formula: (a) 1.67 parts by volume of the Treated MLV-DPCs, (b) 10 parts of SURFAGENE S30 (disodium laureth-3 sulfosuccinate), (c) 17.5 parts of GENAPOL ® AMS (TEA-PEG-3 cocamide sulfate), and (d) 3 parts of EMPILAN CDE (cocamide DEA from Albright & Wilson Ltd. at 100% active content) to obtain Example 23. FIG. 13 is a 400× visible light microphotograph of Example 23 after 6 days at room temperature showing the same type of results as in FIG. 12 and confirming that vesicles were present in Example 23.

Figure 14:
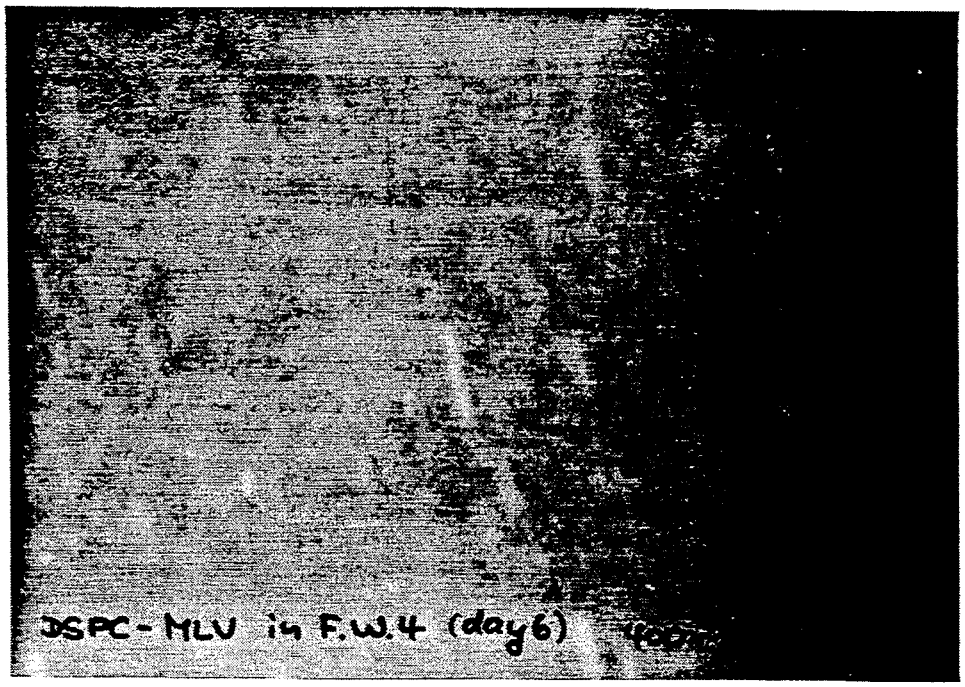
FIG. 14 is a 400× visible light microphotograph of aqueous dye-containing surfactant-treated multilamellar liposomes in detergent solution containing an anionic surfactant known to lyse liposomes taken 6 days after preparation.

Example 24 was prepared in the same manner as Example 22 (additions made in the order listed), but had the following formula: (a) 1.67 parts by volume of the Treated MLV-DPCs, (b) 22.5 parts of SURFAGENE S30 (disodium laureth-3 sulfosuccinate), (c) 11.11 parts of sodium laureth-2 sulfate added as a 28% active content solution, and (d) 6.67 parts of REWOTEIN CPT (TEA-coco-hydrolyzed animal protein from Rewo Chemische Werke G.m.b.H at 25% active content) to obtain Example 24. FIG. 14 is a 400× visible light microphotograph of Example 24 after 6 days at room temperature showing the same type of results as in FIG. 12. Although FIG. 14 is somewhat blurred due to the exposure period used, it confirmed that vesicles were present in Example 24 despite the presence of an anionic lysing surfactant.

EXAMPLE 25

In this comparative Example, the effect on MLV-DPCs of a commercial surfactant blend recommended for use in mild shampoo formulations was tested. In Patent Cooperation Treaty International Publication No. WO 90/01921 to Wallach published on Mar. 8, 1990 (U.S. Pat. No. 4,942,038 issued on Jul. 17, 1990 is the parent application), paucilamellar lipid vesicles are used to encapsulate humectants for addition to shampoos or cream rinses. Wallach's Examples 2 and 3 teach shampoos which are based upon 1 part of an amphoteric surfactant, cocamidopropyl hydroxysultaine, per 10 parts of a commercial surfactant blend from Miranol, Inc. of Dayton, N.J. sold under the designation "MS-1" which the manufacturer reports is composed of 19.4% PEG-80 sorbitan laurate, 17.2% sodium trideceth sulfate (70%), 5.0% PEG-150 distearate, 5.2% cocamidopropyl hydroxysultaine, 10.6% lauramphodiacetate, 2.0% sodium laureth-13 carboxylate, 0.1% Quaternium 15, and 40.5% water. Sodium trideceth sulfate is an anionic surfactant of the class which is known to lyse liposomes. Wallach teaches that his paucilamellar vesicles containing the humectant remain stable in the shampoo formulation.

In this Example, 20 microliters of MLV-DPCs containing dye was added at room temperature to 2 ml of the MS-1 surfactant blend. The solution instantly changed to a bright yellow and the fluorescent intensity increased sharply. This indicated that the liposomes had been lysed, thereby releasing the dye encapsulated within the MLV-DPCs. Examination under a microscope under 400× magnification confirmed that essentially no liposomes were present.

EXAMPLE 26

In this Example, the substantivity to the skin of liposomes treated according to the method of the present invention and applied from a facial wash detergent solution was determined using a radioactive isotope tracer method.

Aqueous liposome suspensions were prepared by mixing 25 milligrams of dipalmitoyl phosphatidylcholine and 3 milligrams of cholesterol in chloroform. A trace amount of tritiated ($H^3$) dipalmitoyl phosphatidylcholine and $C^{14}$-cholesterol were added to the chloroform solution before evaporating the mixture to dryness. The liposomes were formed by gently swirling 3 ml of an isotonic aqueous TRIS buffer solution at pH 7.4 in the flask containing the dried mixture. The large liposomes which were believed to be formed by the gentle swirling were sonicated using a probe sonicator in the pulsed mode for 15 minutes with a minimal amount of cooling. It was expected that SUVs should have been produced, but this could not be confirmed due to the radioactivity of the liposome suspension and the small size of the vesicles. The tracer-containing liposome suspension was treated by adding 1 ml of aqueous SURFAGENE S30 to 3 ml of that tracer-containing liposome suspension to obtain "Liposome Suspension A".

The experiment employed two solutions, one was the "Control Composition" which was prepared by mixing 1 ml of Liposome Suspension A with 1 ml of buffer solution at room temperature.

The other solution ("Test Composition") was prepared by mixing, at room temperature, 1 ml of Liposome Suspension A with 1 ml of a surfactant solution having the following composition: (a) 25 parts of SURFAGENE S30, (b) 13.33 parts of REWOTEIN ® CPK and (c) sufficient deionized water to obtain 100 parts by volume of the surfactant solution.

One milliliter of the Control Composition was applied to 30 square centimeters of human cadaver skin and rubbed for 1 minute. One milliliter of the Test Composition was applied to a different 30 square centimeter section of human cadaver skin and rubbed for 1 minute. The solutions were removed from each section of skin and 25 millimeter ("mm") diameter circles of skin were punched out at time periods of 6, 16 and 32 minutes from application of the composition to the skin. Each 25 mm circle was rinsed for 15 seconds in three consecutive water rinses (i.e., 45 seconds total rinse time). A 6 mm diameter punch was removed for sectioning and the remainder was dissolved in 1 ml of SOLUENE 350 (an alkaline solution for dissolving tissue from Packard Instrument Company of Downers Grove, Ill. at 60° C. for 2 hours. The radioactivity of the dissolved tissue was measured in a scintillation counter using INSTA-GEL from Packard as the scintillator and acetic acid to control the chemiluminescence of the sample. Data from the 6 mm punches (aimed at determining penetration of the liposome suspensions) was deemed inconclusive due to difficulties in handling the punch biopsies.

The following data was obtained from the scintillation counter on the solutions obtained from the 25 mm circles of skin:

| Composition | Time (min.) | Tritium (dpm/%[1]) | Carbon[14] (dpm/%[1]) | $H^3/C^{14}$ |
|---|---|---|---|---|
| Control | 0 | 4644600 | 3416100 | 1.36 |
| Control | 6 | 20777/2.81% | 16094/2.95% | 1.29 |
| Control | 16 | 27424/3.70% | 21396/3.93% | 1.28 |
| Control | 32 | 7660/1.03% | 15125/2.78% | 0.51 |
| Test | 0 | 4259500 | 3141500 | 1.36 |
| Test | 6 | 10358/1.53% | 7846/1.57% | 1.32 |
| Test | 16 | 11278/1.66% | 9012/1.80% | 1.25 |
| Test | 32 | 29445/4.34% | 23663/4.72% | 1.24 |

[1]First entry is disintegrations per minute ("dpm" and second entry is percentage of dpm relative to dpm at time = 0 minutes.

Based on the assumption that liposomes were present in each composition, the data above shows there was an increase in the amount of radioactivity which binds to the skin as time passes. The large change in $H^3/C^{14}$ ratio for the 32 minute point for the Control Composition indicates a breakdown of the liposome structure since ratio should remain relatively constant if the tritiated ($H^3$) dipalmitoyl phosphatidylcholine and $C^{14}$-cholesterol remain associated with each other, i.e., the liposomes remain stable. The $H^3/C^{14}$ ratio for the Test Composition remained essentially constant and there was evidence that liposomes were delivered to the skin despite the fact that the Test Composition contained surfactants and was rinsed away.

EXAMPLE 27

In this Example, the shampoo formulation of Example 15 of U.S. Pat. No. 3,957,971 to Oleniacz was prepared to determine if liposomes were present in the shampoo. Oleniacz teaches a humectant-loaded liposome-containing shampoo containing an amine oxide surfactant in addition to an anionic surfactant known to lyse liposomes, triethanolammonium lauryl sulfate. Example 15 of Oleniacz teaches that "[t]he shampoo is prepared by merely mixing the four components together at room temperature, maintaining the pH between 5 and 6, until the solid components have dissolved . . ." Thus, unlike the present invention, Oleniacz does not recognize there may be a critical order of mixing if one desires to stabilize the liposomes with a surfactant nor did Oleniacz recognize that certain surfactants may serve to stabilize liposome suspensions in the manner discovered by us.

Liposomes were prepared according to the teachings of Example 1 of the Oleniacz Patent from a mixture of egg lecithin, dicetyl phosphate and cholesterol in a molar ratio of 7:2:1 which was dissolved in chloroform and a minimal amount of methanol. The membrane components were dried to a film. Liposomes were formed by hydrating the film with a solution of 0.135 Molar aqueous sodium pyroglutamate and 0.01 Molar aqueous 5(6)-carboxyfluorescein to obtain a 0.145 Molar concentration of additives. The latter was added to assist in showing the existence and integrity of any liposomes present by the methods described above. After preparation, the liposome suspension was left in a refrigerator at 5° C. overnight. The pH of the resulting liposome suspension was about 7.0 and no attempt was made to adjust it to pH 5-6 because at lower pH values, the liposomes are less stable and the dye is less soluble.

The next day, the liposome suspension was placed in a dialysis membrane for 5 hours during which time the 800 ml of 0.145 Molar aqueous sodium chloride solution surrounding the bag was exchanged 4 times. This procedure was needed to remove the dye even though Example 15 of Oleniacz stated that no dialysis of the liposome suspension was used. At the end of this time, the untrapped dye had not been sufficiently removed, but the dialysis procedure was terminated to follow Example 1 of Oleniacz while still removing as much as possible of the dye from the external aqueous phase. The liposome suspension contained 0.0602 grams of solid components of the liposome material in 50 ml of the aqueous sodium pyroglutamate solution (0.12% weight/volume).

The microscopy method specified by Oleniacz is cross-polarized light. With this method, liposomes were clearly observed in the suspension removed from the dialysis bag at 400× magnification. Cross-polarized light only shows objects with ordered molecular structures, such as the lamellar bilayer structure of the liposomal membranes. The liposomes appeared as bright, round dots against a dark background. As a control, 400× micrographs of the formulations described below were taken before the liposome suspension was added since other types of molecular structures commonly found in emulsions can easily look quite identical to liposomes.

Since Oleniacz does not specify any particular order of addition, two formulations were prepared using different orders of addition. The first order of addition ("Shampoo 1") was to add the ingredients in the order listed in Example 15:20% of SIPON ® LT-6 (40% active triethanolammonium lauryl sulfate from Alcolac, Ltd. of Quebec, Canada); 20% of 95% ethanol; 5% of AROMOX ® C/12 (50% active bis(2-hydroxyethyl) cocamine oxide from Akzo, Chemical Division of Chicago, Ill.); and 55% aqueous liposome suspension as prepared above. "Shampoo 2" was prepared by adding the SIPON ® LT-6 to the AROMOX ® C/12 and separately adding the ethanol to the liposome suspension. The surfactants were then added to the ethanol/liposome suspension.

A detergent composition ("Detergent 1") of the present invention was prepared by adding 45% of an aqueous solution containing 25% SURFAGENE S30 and 13.33% REWOTEIN CPK to 55% of the liposome suspension prepared above.

The results of a cross-polarized visible light microscopic examination at 400× magnification of the above were that structures appearing to be liposomes were abundant and clearly visible in both the liposome suspension and in Detergent 1. Examination of Shampoos 1 and 2 showed extremely few bright spots for each formulation which might or might not have been liposomes, but the number of bright spots in each was much less than was seen for the liposome suspension and for Detergent 1. Microphotographic examination of the liposome suspension after addition of ethanol, but with no other surfactants, showed the presence of very small bright spots which might have represented crystalline materials. The Shampoo 1 and 2 components as well as the Detergent 1 aqueous solution were each microscopically examined as controls before addition of the liposome suspension. No bright spots of the type seen with the liposome suspension were observed. The controls were necessary because liquid crystalline materials may appear as bright spots under cross-polarized light and emulsions not containing liposomes might also contain such materials which might be mistaken for the presence of liposomes.

What we claim is:

1. A method of making a detergent composition containing liposomes and anionic surfactants which lyse liposomes which method comprises the steps of
    (I) preparing a stabilized aqueous liposome suspension by adding from about 0.1% to 40% by weight based upon the total weight of the stabilized aqueous liposome suspension of at least one surfactant selected from the group consisting of fatty alkyl sulfosuccinates where the fatty alkyl group contains from 8 to 22 carbons atoms, fatty acylamino polyglycol ether sulfates where the fatty acyl group contains from 8 to 22 carbon atoms, fatty alkyl amine oxides where the fatty alkyl group contains from 7 to 26 carbon atoms, fatty alkyl phosphate esters where the fatty alkyl group contains from 8 to 22 carbon atoms, and N-acyl amino acid salts or salts of N-acyl derivatives of hydrolyzed proteins of up to about 2,500 daltons in weight average molecular weight where the acyl portion is derived from a carboxylic acid having from 8 to 22 carbon atoms per molecule to an aqueous liposome suspension containing from about 0.1% to 50% by volume of liposomes based upon the volume of the total aqueous liposome suspension and the ratio of the liposomes to the surfactant present being in a ratio of no greater than 30 parts by volume of liposomes to 1 part by weight of surfactant; and (II) Adding to the stabilized aqueous liposome suspension of step (I) from about 0.1 to 35% by weight of the total detergent composition of at least one anionic surfactant which is known to lyse liposomes to form an aqueous detergent composition containing liposomes wherein the liposomes are observable in the detergent composition for at least 48 hours after storage at 22° C.

2. The method as claimed in claim 1 wherein the surfactant of step (I) is at least one surfactant selected from the group consisting of
(a) $R^1(OCH_2CH_2)_aOC(O)CH(SO_3X)CH_2C(O)OX$;
(b) $R^2(OCH_2CH_2)_aC(O)CH(SO_3X)CH_2C(O)OR^1$;
(c) $R^1C(O)NH(CH_2)_bOC(O)CH(SO_3X)CH_2C(O)OX$;
(d) $R^1NHC(O)CH(SO_3X)CH_2C(O)OX$;
(e) $R^3C(O)NH(CH_2CH_2O)_cSO_3X$;
(f) $R^3R^4R^4N\rightarrow O$;
(g)

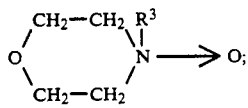

(h) $R^5C(O)NH(CH_2)_dR^4R^4N\rightarrow O$;
(i) $(R^1(OCH_2CH_2)_aO)_eP(O)(OZ)(OH)_{2-e}$; and
(j) N-acyl amino acid salts or salts of N-acyl derivatives of hydrolyzed proteins of up to about 2,500 daltons in weight average molecular weight where the acyl portion is derived from a carboxylic acid having from 8 to 22 carbon atoms per molecule wherein $R^1$ is an alkyl group having from 8 to 22 carbon atoms, $R^2$ is an alkyl group having from 4 to 16 carbon atoms, $R^3$ is an alkyl group having from 8 to 18 carbon atoms, $R^4$ is an alkyl group having from 1 to 4 carbon atoms or $-C_fH_{2f}OH$, $R^5$ is an alkyl group having from 7 to 26 carbon atoms, X is an anion, Z is —H or X, a has a value of from 0 to 8, b has a value of from 1 to 4, c has a value of from 1 to 6, d has a value of from 1 to 5, e has an average value of between 1 and 2, and f has a value of 2 or 3.

3. The method as claimed in claim 1 wherein the anionic surfactant added in step (II) is selected from the group consisting of at least one anionic surfactant of the general formula $R^6(OCH_2CH_2)_gQ$ where $R^6$ is selected from the group consisting of alkyl groups of from 8 to 18 carbons atoms, phenyl groups, and alkaryl groups of from 6 to 24 carbon atoms, g has an average value of from 0 to 10 and Q is selected from the group consisting of —C(O)OZ, —OSO_3Z and —SO_3Z.

4. A method as claimed in claim 1 wherein the surfactant used in step (I) is used in an amount of from about 0.1% to 35% and the surfactant used in step (II) is used in an amount of from about 5% to 15% by weight.

5. The method as claimed in claim 1 wherein the liposomes are formed from at least one phospholipid or nonionic amphiphilic compound.

6. A stabilized detergent composition containing liposomes formed by the method of claim 1.

7. The detergent composition as claimed in claim 6 wherein the liposomes are formed from at least one phospholipid or nonionic amphiphilic compound.

8. The method as claimed in claim 1 wherein the amount of anionic surfactant added in step (II) is at least 5% by weight of the total detergent composition.

9. A stabilized detergent composition containing liposomes formed by the method of claim 8.

10. The method as claimed in claim 1 wherein the amount of surfactant added in step (I) is from 2% to 10% by weight based upon the total weight of the stabilized aqueous liposome suspension, the amount of anionic surfactant added in step (II) is from 5% to 15% by weight of the total detergent composition, and the liposomes are formed from at least one phospholipid or nonionic amphiphilic compound.

11. A stabilized detergent composition containing liposomes formed by the method of claim 10.

12. A method of making a detergent composition containing liposomes and anionic surfactants which lyse liposomes which method comprises the steps of
(I) preparing a stabilized aqueous liposome suspension characterized by adding from about 0.1% to 40% by weight based upon the total weight of the stabilized aqueous liposome suspension of at least one surfactant selected from the group consisting of
(a) $R^1(OCH_2CH_2)_aOC(O)CH(SO_3X)CH_2C(O)OX$;
(b) $R^2(OCH_2CH_2)_aC(O)CH(SO_3X)CH_2C(O)OR^1$;
(c) $R^1C(O)NH(CH_2)_bOC(O)CH(SO_3X)CH_2C(O)OX$;
(d) $R^1NHC(O)CH(SO_3X)CH_2C(O)OX$; and
(e) $(R^1(OCH_2CH_2)_aO)_eP(O)(OZ)(OH)_{2-e}$;

wherein $R^1$ is an alkyl group having from 8 to 22 carbon atoms, $R^2$ is an alkyl group having from 4 to 16 carbon atoms, X is an anion, Z is —H or X, a has a value of from 0 to 8, b has a value of from 1 to 4, and e has an average value of between 1 and 2, to an aqueous liposome suspension containing from about 0.1% to 50% by volume of liposomes based upon the volume of the total aqueous liposomes composition and the ratio of the liposomes to the surfactant present being in a ratio of no greater than 30 parts by volume of liposomes to 1 part by weight of surfactant; and (II) Adding to the stabilized aqueous liposome suspension of step (I) from about 0.1 to 35% by weight of the total detergent composition of at least one anionic surfactant which is known to lyse liposomes for form an aqueous detergent composition containing liposomes wherein the liposomes are observable in the detergent composition for at least 48 hours after storage at 22° C.

13. A stabilized detergent composition containing liposomes formed by the method of claim 12.

14. The detergent composition as claimed in claim 13 wherein the liposomes are formed from at least one phospholipid or nonionic amphiphilic compound.

15. The method as claimed in claim 12 wherein the amount of anionic surfactant added in step (II) is at least 5% by weight of the total detergent composition.

16. A stabilized detergent composition containing liposomes formed by the method of claim 15.

17. The method as claimed in claim 12 wherein the amount of surfactant added in step (I) is from 2% to 10% by weight based upon the total weight of the stabilized aqueous liposome suspension, the amount of anionic surfactant added in step (II) is from 5% to 15% by weight of the total detergent composition, and the liposomes are formed from at least one phospholipid or nonionic amphiphilic compound.

18. A stabilized detergent composition containing liposomes formed by the method of claim 17.

* * * * *

UNITED STATES PATENT AND TRADEMARK OFFICE
CERTIFICATE OF CORRECTION

PATENT NO. : 5,328,628
DATED : July 12, 1994
INVENTOR(S) : Gerald L. Hart, Anjum F. Ahmed & Ursula K. Charaf It is certified that error appears in the above-identified patent and that said Letters Patent is hereby corrected as shown below:

In column 24, line 45, "for" should be --to--.

Signed and Sealed this

Twenty-first Day of March, 1995

Attest:

BRUCE LEHMAN

Attesting Officer           Commissioner of Patents and Trademarks